(12) United States Patent
Yoon et al.

(10) Patent No.: US 11,679,137 B2
(45) Date of Patent: Jun. 20, 2023

(54) VIBRIO PARAHAEMOLYTICUS BACTERIOPHAGE VIB-PAP-4 AND USE THEREOF IN INHIBITING PROLIFERATION OF VIBRIO PARAHAEMOLITICUS BACTERIA

(71) Applicant: Intron Biotechnology, Inc., Gyeonggi-do (KR)

(72) Inventors: Seong Jun Yoon, Seoul (KR); Soo Youn Jun, Seoul (KR); An Sung Kwon, Gyeonggi-do (KR); Hyun Min Song, Seoul (KR); Soon Hye Hwang, Gyeonggi-do (KR); Sang Hyeon Kang, Seoul (KR)

(73) Assignee: Intron Biotechnology, Inc., Gyeonggi-do (KR)

( * ) Notice: Subject to any disclaimer, the term of this patent is extended or adjusted under 35 U.S.C. 154(b) by 587 days.

(21) Appl. No.: 16/471,051

(22) PCT Filed: Nov. 29, 2017

(86) PCT No.: PCT/KR2017/013765
§ 371 (c)(1),
(2) Date: Jun. 19, 2019

(87) PCT Pub. No.: WO2018/117462
PCT Pub. Date: Jun. 28, 2018

(65) Prior Publication Data
US 2019/0328803 A1    Oct. 31, 2019

(30) Foreign Application Priority Data
Dec. 21, 2016    (KR) ........................ 10-2016-0175223

(51) Int. Cl.
*A61K 35/76*    (2015.01)
*A23K 10/18*    (2016.01)
(Continued)

(52) U.S. Cl.
CPC .............. *A61K 35/76* (2013.01); *A23K 10/18* (2016.05); *A61K 9/0014* (2013.01);
(Continued)

(58) Field of Classification Search
None
See application file for complete search history.

(56) References Cited

U.S. PATENT DOCUMENTS

| 9,504,721 | B2 | 11/2016 | Sung |
| 2013/0323209 | A1 | 12/2013 | Sung |
| 2015/0306159 | A1* | 10/2015 | Yoon .................... A23K 20/195 435/235.1 |

FOREIGN PATENT DOCUMENTS

| KR | 10-2013-0021677 A | 3/2013 |
| KR | 10-2014-0000541 A | 1/2014 |
| KR | 10-2015-0024115 A | 3/2015 |

OTHER PUBLICATIONS

World Health Organization, "Risk assessment of Vibrio parahaemolyticus in seafood: interpretative summary and technical report", World Health Organization, 16, 1-183 (Year: 2012).*

(Continued)

*Primary Examiner* — Michelle F. Paguio Frising
*Assistant Examiner* — Grant C Currens
(74) *Attorney, Agent, or Firm* — Ballard Spahr LLP

(57) ABSTRACT

The present invention relates to *Myoviridae* bacteriophage Vib-PAP-4(Accession No. KCTC 13168BP), isolated from nature, which possesses ability to specifically kill *Vibrio parahaemolyticus* bacteria and has the genome represented by SEQ ID No: 1, and a method for preventing infection of *Vibrio parahaemolyticus* bacteria and treating infection of *Vibrio parahaemolyticus* baceteria, using a composition containing the bacteriophage as an effective ingredient.

1 Claim, 1 Drawing Sheet
Specification includes a Sequence Listing.

(51) Int. Cl.
*A61P 31/04* (2006.01)
*C12N 7/00* (2006.01)
*A61K 9/00* (2006.01)

(52) U.S. Cl.
CPC ............ *A61K 9/0056* (2013.01); *A61P 31/04* (2018.01); *C12N 7/00* (2013.01); *C12N 2795/10133* (2013.01); *C12N 2795/10171* (2013.01)

(56) References Cited

OTHER PUBLICATIONS

Richards, G.P, "Bacteriophage remediation of bacterial pathogens in aquaculture: a review of the technology", Bacteriophage, 4(4), 1-12 (Year: 2014).*

Stalin, N. et al., "Characterization of Vibrio parahaemolyticus and its specific phage from shrimp pond in Palk Strait, South East coast of India", Biologicals, 44(6). 526-533 (Year: 2016).*

Office Action dated Dec. 15, 2020 by U.S. Patent Office for U.S. Appl. No. 16/064,725, filed Jun. 21, 2018 and published as US 2019/0000897 on Jan. 3, 2019 (Inventor—Yoon et al.; Applicant—Intron Biotechnology, Inc.) (8 pages).

Notice of Allowance dated Feb. 3, 2021 by U.S. Patent Office for U.S. Appl. No. 16/064,725, filed Jun. 21, 2018 and published as US 2019/0000897 on Jan. 3, 2019 (Inventor—Yoon et al.; Applicant—Intron Biotechnology, Inc.) (7 pages).

KR, 10-2016-0175223 (10-2018-0072055), Dec. 21, 2016 (Jun. 29, 2018), Seong Jun Yoon (Intron Biotechnology, Inc.).

PCT, PCT/KR2017/013765 (WO 2018/117462), Nov. 29, 2017 (Jun. 28, 2018), Seong Jun Yoon (Intron Biotechnology, Inc.).

Office Action dated Jan. 20, 2022 by U.S. Patent Office for U.S. Appl. No. 16/611,877, filed Nov. 8, 2019 and published as US 2021/0138005 on May 13, 2021 (Inventor—Yoon et al.; Applicant—Intron Biotechnology, Inc.) (21 pages).

Office Action dated May 9, 2022 by U.S. Patent Office for U.S. Appl. No. 16/611,877, filed Nov. 8, 2019 and published as US 2021/0138005 on May 13, 2021 (Inventor—Yoon et al.; Applicant—Intron Biotechnology, Inc.) (15 pages).

Jun, J.W. et al., Bacteriophage Therapy of a Vibrio parahaemolyticus Infection caused by a Multiple-Antibiotic-Resistant O3:K6 Pandemic Clinical Strain. J Infect Dis. 2014; 210(1):72-8.

NCBI, GenBank Accession No. JQ692107.1. *Vibrio vulnificus* Phage SSP002, Complete Genome. 2012, pp. 1-39.

NCBI, GenBank Accession No. JX556418.1. *Vibrio* Phage vB-VpaS_MAR10, Complete Genome. 2012, pp. 1-43.

Villa, A.A. et al., Genome Sequence of Temperate Vibrio parahaemolyticus Bacteriophage vB_VpaS_Mar. 10. J Virol. 2012; 86(24):13851-2.

International Search Report and Written Opinion dated Dec. 10, 2018 by the International Searching Authority for Patent Application No. PCT/KR2017/013765, which was filed on Nov. 29, 2017 and published as WO 2018/117462 on Jun. 28, 2018 (Inventor—Yoon et al.; Applicant—Intron Biotechnology, Inc.) (Original—10 pages; Translation—5 pages).

* cited by examiner

[FIG. 1]
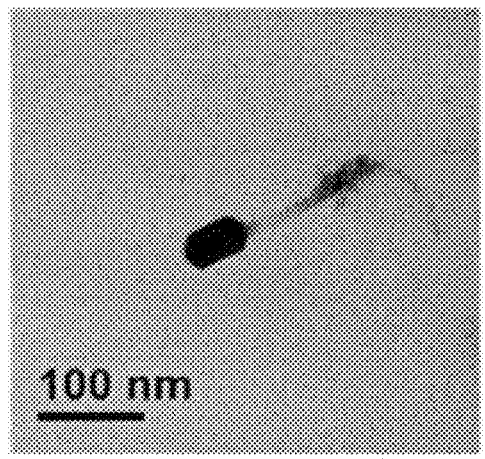
[FIG. 2]
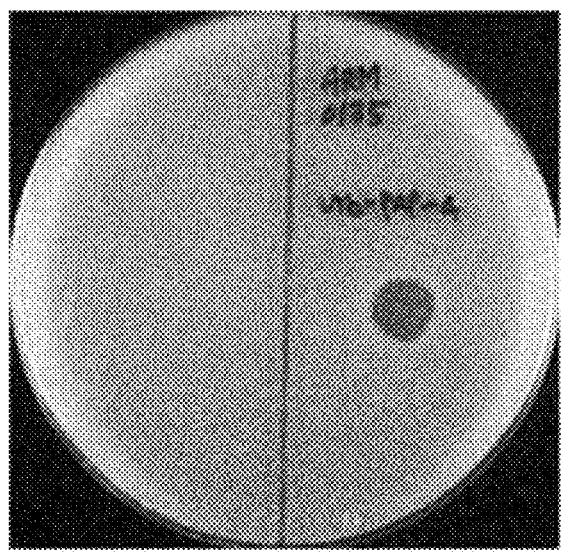

SEQUENCE LISTING

<160> NUMBER OF SEQ ID NOS: 1

<210> SEQ ID NO 1
<211> LENGTH: 76666
<212> TYPE: DNA
<213> ORGANISM: Vibrio parahaemolyticus bacteriophage Vib-PAP-4

<400> SEQUENCE: 1

```
aaaaatttta cctaggaggt ttgaaaaatt ttacctagga ggtttgggat tctggtggga      60
tttcggaccg tggagatgcc aaaccacttg agaagatttt acatcttttc acttgacttg     120 agatctttt  atatctttt  aggttttctt ccgggcatag catagccggg atcgttagta     180
aacccctttt agtaaatttt atgttttcca cttccaccgg gaagcggtcc cggcgtggaa     240
ggcgtcgcca gctggaccgg gaacccggca accgggcaac cgggaaggcg tccccgttgt     300
ggtgcctatt accacaaatt gcggatcaac taccaaacac tttttaatag tttttagtaa     360
taagcatata acaatttaat ttactaaaat gattgaagtt gcccgccgtt tttagtaaac     420
gcgtgcgccc ggtctattta ccattagtaa aaaaataatt gttgaaagtt taaaaaaggt     480
attgtaaccg ggagcgggtt ttagtaagat gtatcacaag gaaggcggga agggttcccg     540
gctatggcaa acaatggagc gccgatcatg tttatagatt tgaacaaagt tgtactactt     600
cccaactttg attggatgtt ttggaccggg atcgcgtgcg ccgcttatat cgtttggaaa     660
ttctcaaaat gaaaatatta ctaatttgtg ccgttatcgc tggcggtcta gtatcatgcg     720
atcaagttat gaccgctaac gccgtgaaaa cgtgcgaggc taaaaagcaa gccggggaat     780
tgtccgcacc tttaacaac  tgtgatattt tgaaatttta gtaaaaataa ttgttgaaag     840
ttgcattttc ctattgtacc cggaccgggt ttttagtaat ataaccatat cgaagcaaac     900
aaacatttaa ggatgtcact tatgtttaac cgtcaaactc aaaaacaaaa gatcttttcg     960
ttagcgtggg acaatgctcg ccacgctgca aacttccacg gcggcgagcc ccgcgaatat    1020
ttcgcggaat ctctaaagct tgcttaccgt ggcgtaaaac tggcaaacgt aaaaccacga    1080
tctgaagttt tcacactgga tctagttagc gcggttttgt gtggcatcct tgcaatagca    1140
ataattctct tttcaatctg gatcggtcat ccagcggcta ttctatccgc gcttatcggt    1200
ttggcaatcg gtgccgctgg ttggtctgat ttcgaactgc acttgcaaga aattgcagaa    1260
aacaaacgaa tcaataaaaa tactaatttt aaccgtctag taattgactt ttaagtaagg    1320
gcataccatg cgcaatctaa acaactattt ttctattgaa caaaaactta ctaaccgcac    1380
ggaagcggta aacactgcaa accgttttat taacgaagtt gcgcccgttc tgatcgctcg    1440
cctatctgaa ggcttcaaga tcaaaaccac gtcaaatgat ttctttaaaa aggatcacga    1500
cgacttgaga tccatcctcg ataacgcggc gacggcgggc aagattcatc aagcttttt     1560 agatgttacc gacacggtga tccgcgtccg cgtgaaaaca acgttttcag tcagtgaggt    1620
tggttgctgc tatcatgagg actttgtcaa tatttggagc cgtgaaaaag atcaggcgtg    1680
ggacttccag ccgctggaga ttatcccggt tggaaaagtg atcgaagcgc atcaagcgat    1740
```

```
caaaccactt gaagatcaga tccgcgaact taaagcgaaa ctatctcaac ttaaatcaat      1800
tacgggcggg ctataatcat ggatctatca actaacatct atgcagcgga taaccgttac      1860
cacttttcgg atcgctatga tgagcacggg accttaaacg atctagcgtg tgagtacgcg      1920
gataaattcc agtccgaata cttggagcac atcaacggcg agaccgccga tcccgacgac      1980
gctcaaacgt tagcgcatga ttacgcccgc gaaactgtac tcgatggaat gtgccgtttt      2040
agtgttcgct ttttcgcggt cacttacccg gatcatgttt tgacgcgtaa accattcgat      2100
acacttggag ccgaaacacc ggatcagcta atccgccgaa atattgaaga agttgtgacc      2160
gccgccgcca acgtcctgat cgaagaaatg cgcgagcgtg gagatcttga ccgtgacgaa      2220
tagcattgaa gcattgacgg atcgcggata ccttccagcc ggggagttta acccggctat      2280
tcataaaaag gttagtaaat gcgatttggg cgggatacct tgccgcgtgg ttagcggtcc      2340
cggcttggag cgcgggatca tgccatacca cacaacaaag atgatcggcg gcttcccggt      2400
agtggtagac aataaaacat attttgtaaa atcgaattag taagggcgtt actatgaaaa      2460
aggttaataa accacaatca aaccgattct ttgaaggcgt gcgagatctt gacagcctga      2520
tcgggcgttc gactcacaac ggcgagtatt caaacaatgt gatccgttta gggttcacac      2580
atttaaacgg tcaagtgttg aaggttgcc cggtttatat caccggggaa ttgttcgaca      2640
aaatcggcgg gatggtttac ggcaacggcg gcgaactaaa caagcgttac cgcttggaga      2700
tggtttacac aatgggcggc gaatatcatc tttttgtcaa gtaccagcac attaacggat      2760
cgcgtcgtgt ttgtgcaata tccccggata gcgtccagcg atggatcgac acgcaaccga      2820
aaagcaatta atttaaattc tattagtaag ggcgcatttt gcgcccttt ttgtacccgg      2880 taagctgtac agcttttatta ctaatattta gcttttgct gtacgtgcag cggcgatcta      2940
gggcgatttt tcaatttggc gcgaaacgaa gcttttaata ccatagcaag gcttttacta      3000
aaaaccgctt acaacgccat acagcgcgaa tttgtggcat attactaaaa cgtgttttag      3060
taattactat tagtaaaaag agttataaaa ataattgttg aaagttggtt tttcctattg      3120
tacccggacc gggtttttag taatatgtat cacaaggaag gcgggaaggg ttcccggcta      3180
gattgtgtgg agtgctcgca atggcatcac aaaaacttga tattttcccg gctcgcttgg      3240
gtttaccgtc gcaactaaac aaggctttta aaaaggcggg tttatccgtt gtcatattgg      3300
ataagcatcc acgcggatca gttgctagcc gtggcgatca aaatttcgtt tgctaccgtg      3360
ttgattttaa atccgttagt aagtgcggcg atggttccga cgctcgcccg gcttcaatgg      3420
cattcactca caacacaaaa acgcaccgcg tgacgttaac agaaatcgac tatctttaat      3480 ttatatttt atcagtaagg gctttacaat gacagttact aaactagaag cattaaaaac      3540
aactttcgat caagcggcaa acgcggcaat cgacgcgggc gcaactcatt acattatcaa      3600
taaaacgctg tacgcgggac aatggatcac gttctcttat agttttgtta attgcgacaa      3660
aaagaaactt aatcaagttt ttgaagttgg gacgtatatc aaagagatga aaacatacac      3720
accaacggat cgttggatgt ctgacaagtg gatcgggcat aacctagacg ggcgagaccg      3780
ccacggaatg atcaattctg aattgttcca gctggatcgc ggtattatta agtaatcaca      3840
caataacaac tattcacaca tttattagta agggcttatt atgaaaacta tttgtaaagt      3900
tatcgcggga tcattcgctg gcgagtttgg tcgccttcat tctaaattca gcacgggctt      3960
gatcatgctg gaggaccgcc acggcgatca gttgtctgtc actgaaaagc agatcgaacg      4020
cttggaagtg cgcacggcta acctaaacaa tccaactatt caaggtttga ttgatattga      4080
```

```
tggatctatc aagtacggct tcaatagtgg cggctacgaa tcaaacgcgt actttatcac    4140
ggcggacggc ggcacgctgg caattaatac agttatcagt gagatcgata aagttgattt    4200
ctgcgacgac tgcgatccgc aatggcatat tgtacaccac ggcgtaaact atgaagagac    4260
ggatctttta gactctcaca cgggcgaacc aatcccggcg gcgtacagtg acgacgacta    4320
aaaacaatta tattagtaag ggcgcatttt gcgcccttt ttgtatccgg gaccgcgtac    4380
agctttatta gtaaataact gcttttcgct gtacgtacac cggggatcta gggcgatttt    4440
tcaatttagg gcgaaacgcg gcttttaata ccatagtaag gatattagta aaaaccgctt    4500
aaaacgccat acagcgagaa taagagctat attactaaat cgcgtttacc cggtttaata    4560
ttagtaaaaa cgttataaaa ataattgttg aaagttggtt tttcctattg tatccggtcc    4620
gctaatttag taatatattc acacggtaag agattaccaa tattaatcat tttccccggt    4680
ggatttcccc ggtttattta gtaagggctt attatgaaaa ctgttaaaat tactaattct    4740
gatttagtgg ctattcgttc aaagtttgat cgcgaacttc aaaagcaaaa agatcgctat    4800
gctgcaaacc cggatttgta cggcaagcaa gcggaagaat cattgcttcc acgctggatc    4860
gataacgctt atagtaaagc agtgtttcaa caattggagc gcgacgggct agcacacatc    4920
aacaaagaat cagattcttt ctactcattc gcggatcatg ctggcgattg cttcgatcct    4980
gaagttaata aagacatcga tccggcggaa ttgaaacgcc agcgtaaaaa cgaattagca    5040
cgattcaacc gtcaaggcgt atactaccat gaattaattg tgctaggcga aacgctagga    5100
tcaataggcg gctttgtggg gaatgacttt tacggatcag gctacgacat tgattttac    5160
aacacggcga tcactcacat tgcgaacgtg tacggcgacg gctttatccc gacactagac    5220
aaaatccaaa aagcaaccgc gcacactgat ttagtaacaa cttctcttta ttgcgattac    5280
tctaaaacag tgcgcacaaa agcgaatcat tgtgtactaa actttttga gcgtgatcac    5340
cgctggattg ttgatattga tcgcggcgtc ccggtagaga tcgcggcact tgttttgag    5400
ttgttccata catcgcatga ttttgtatgg tccaaaactg gcgagcaaaa agcggaaatt    5460
ctaaataaat acatcgcgga caacttgaaa taatcgggag ttactaaaat gcaaaatgtt    5520
tacggttata tctatatgtc tgttttttgt gaaactggtt taagcgaacg cggtgcaaaa    5580
attgccgcgt cccgtgtggg cgcttcccaa gtgggctatc gttcaccgat caataacatg    5640
tatattcaaa cggcggtaaa gaatgccgcc ggaaaatggg aggcgcgcta aaatggaggt    5700
taagatcacc gggcaaaatc caatacataa acacgtgtat tctactttct accgtggcaa    5760
acgcttcgac gtgaacacgc taacaaatag cgttactatt gcgactttta acgataagac    5820
gggatcgcgc ttcctcccgg ttaaatcttc agttactaaa aacaaagtat tgagcgccgt    5880
actacaacac atcgcaggca ataaggatca ataaaatgtc attacgtgga attgcacaaa    5940
ctgaaatcga atcgtacaac gcgctgatcg ttctaatcga aaacggcgaa cactcaaaag    6000
cgcgtgcaat gttttgcgat tgggaccaat caaaacaaag tcgtttatc cgtgcgcttg    6060
gagatcttga aggcgtgaca cttgaattac atcttgaaac attaaagcaa ttgattgttt    6120
tgtatgttta gcaaatttac actgtaaacc attatttatc attttattag taaggaaaaa    6180
gttatcatgt ttaatcaagt tattgttgaa attccagcgg gcgagatcat cacgcgttgaa    6240
acttataaca cgccatatca ggcacgcggg atcgctcgct gcattcaagc ggttgcgggt    6300
actgattacc aaccgggcaa aaactatttt gttcacgtcc caagttcaca aattaaccgc    6360
gaggcgttcg aatacatcac gtctattgat ttagcaatta ttgttagtgt tgctaatagt    6420
aatccggcgg gcgtcactgc aattgatgcc gagcatcagg aaaccgttaa tagttttatc    6480
```

```
aattggaaca acgatcaccg tctagccgtt gaagcggata agcgcgaatc aacacttgaa    6540
acacgcttac acaaatctaa atgctatcag caagcggttt acttttggcg taaccttcca    6600
ctaagtgaga aaataatat tagtaaagta tttccagcac tggcggacgg ctacccgctt     6660
gaatcacaat ttggcggcat tgataaataa atcaatacca ctttacactg taaatcactt    6720
agtaagagat aatcacatta tgagtatcat gattgaaata cacaaggcgg aaaatctaga    6780
tccagaaagt ttcccgttat gcccttattg cgaccaaccg atccaaaacg tacacgacgc    6840
aacgataata tataacggta tgttttccgt tttggcacta gcgcataaaa catgccagca    6900
agaaaacgaa tcacaataat atcaatagtg actacgcccg gtttaatcgc cgggcttttt    6960
attgtctatc gtttactaat aacacattac taaatagtat catttccccg gttgcccttc    7020
ccggttgtat ccgcccgcca gctatccaca cgccgccatt tttcacctcg acataaacgc    7080
gccgcgcaat catatataat gataaatctg tataacaa ttctccctag tgtgtaaata      7140
ctcattatcc tatataggta gctatccgtg tatattcttt atattatgtt atttgttatt    7200
agtgtattta tcattatc tttcttacta atacttttat cattttgcg tatattcccc       7260 atctactgaa gagtaaaaag atagtaagca ttatatcaat aagaaagtgg gcgaaatcgg    7320
ggcgcaaacg ggctatatcc gggcgattgg gcattaaccc atatcatcgc accactacca    7380
cacgcaaacg ggcgcacacg gctttacagc gatgcagtat attgagcatt ctattattag    7440
ttgttcgctc ttactaaaac attgaacaac tagcaacaat aaattataat ctatacacgg    7500
tagggaagcg ggttttccct atatacggaa attcactata tacacattag gcggtcacta    7560
tgtcagatat atactacggt tcgttttgcg cgggcttgtt tgctcttatc gtttacggtt    7620
gtcacttaat gggggcgatg taatgttata ttcattagta atcattctag tattgaatgg    7680
cgagccgcaa tatcatatcg aagattacaa tctatcattt gaggattgtc agcacgcgct    7740
atcacacatc gatcagtcta tcccggcgat gtgtgtatca caatcaggta atgagctata    7800
acacaataac tatttactaa acactcatta ctaaatgccc ggttcacgtc cgggcttttt    7860
tatatccgca attcactata tacaatccta tcagtaacgc cacgcctacc cggaccgatt    7920
gaccgggacc aaccgaccaa cacgcaaacg caatgataca actatcaata gactattgag    7980
cattgcatca ttaccaattc cctattgagc aatcgcacta taaacaaatc tattagtaaa    8040
caattctatc agttgcgcaa atgataatag tgtcattgag taatctgtca gttgcgcaat    8100
tgagtaatct atcaataagg gggtccgaac cccccacccc ccggcacata ttcgacgctt    8160
atccccggca catattcgac gaagcccac cccgtctggg ctggactcc atcggagtgc      8220 cggacggatt ttgtctgcca cgtgttgggg accacgacca acgaccattt actaatggac    8280
ctcgaccaac gaccatttac taatggacct cgaccacgac caccgggacc atcggacaat    8340
gaccgttagt aaatggacca ttggaccgaa ggggtttgta aattatcatg ggggtgtcgt    8400
atagttcgtg gaccaatttt ttccgggacc agttttgaag ttttactaa aacgaggac      8460 cagatgacca gaccgaagag gagattgatt gtagtcgagt accgatgctt ccggggacat    8520
gcccccattc gaattgtgcg gggctctgcg aaggcttccg tatgctatca atgtcatcgt    8580
atgcaaagaa agcacgcacg catggtagca cgctgccaca acccaaagga cccaaggtac    8640
aagaactacg gagggcgcgg gatcagcgta tgcccagaat ggcgtaactc atttactaaa    8700
tggtatgagg acttcggcta cctcgtagat gggaatgacc tgactatgga ccgtagggat    8760
aacgatgggg attacgagcc ggggaatatg cgtgcagcca ctacccaaga gcaaaaccgc    8820
```

-continued

```
aaccaacgaa gaagtgtttt actaacgtac gatggggaga cgctgaatca acaggtgtgg    8880
gcagataggt tcggctttca taaatccagt atacagcgac gccttggtgg gaagtaccgg    8940
aatgatatgg aatgggtact cttttggcgta cgcactacta ttactaaaac ggaggtactg   9000
attactaagg acaggaagcg gttgaacttg cgtgcttggt gtagatctct gggtttctca    9060
ctacgcacag tagaggaccg ggtatacaag ttcggctgga gttatgcgca ggcactcggc    9120
tttgcctccc ggaagggaaa acttagacca ccgcctacaa aggattagta aataatagtt    9180
gcagttagta acactgtggc atatactctt tatacaccaa ctaactaaga aggattagta    9240
aaatgaagga cttcaatatg agcgaggagc ttactcgcgt acaggctggc tggtatgagc    9300
agtctaagga cgccgtgtac aacttgaagg atgttactaa agcactcaca gacggcaagt    9360
cgctaaagca ttgtaagcgc atggtggaag acatccccgg tattggtctc tcccaacgta    9420
cgcaggaata tttgcaggtg ctttgaact gtaaacgcat ggagaacttt agtaaatgct     9480
tgttcaaggc ttaccaaatt caaacgcgta atgcagcaag tctgaagaag gactcgtaga    9540
atggttaaac cgacacaccg cactgtgta gtaacttcta agggtcgtgt accctacgat     9600
gagaagcatt actaccacac tggcaaaaag ggagaggatg ttacgttagt aaacgagcgt    9660
aacttcaaaa cggtacaggg acagcgattc gaccttgtac ttttcgttgg caacatatcc    9720
ggggaagttc gtacgaagtt cgctgggttg gttggagatt actaaaatga aacgcaagta    9780
cttcgacgaa gctttaccat cgttctttgt gttcggggag cacgctaacg gtacggtgga    9840
cctatcgtgc ggtgagtttg atgtagtaac atactgccct accgaaatgg cagaagccgt    9900
catcgcttac tacgacagcc tgttgcttaa gctgcatgag tgggtagtcg atcaggagaa    9960
accctcggaa gccctcgaca aactctgtga cgctttccaa ggtgttcacg cggggcatca   10020
ttacattggc gacttcgggg ctgtaatgtt actaaaactg ctgtgggaag cgtacaccaa   10080
gatagcgaca atcgtccatc cgagattctt acgcagcgtg tacggtgtag agtggacccc   10140
ctcactggtg caggcgaact tactaacgca acgtgggtac accccttact gtggtggtcg   10200
tgactgcaag tcggtccctc gaacagcgtt ccgggaggag cagttccgct gccctagctg   10260
cggttgggag tcgaacttg accctgagtt cattgctggg tacaagtacg tgtgggactt    10320
gccgggagtt gactgcgaga tgctagacga gttccgtgca atactaccac tatcactaca   10380
cttcgtaatg gtagacgcgg acatgagata cgcggggcgc attgatgatg agtaggaagc   10440
gtttaccttt agtaaaacgt acaagcgtac attgggctca gctcaccggg attgtcataa   10500
tggaccccgga tggatgggac cgccagaact tcgaatacag ctggtatgaa gagaccatta   10560
ccattctgga gttctgggat cgcgtgtaca actcaacaac actcatgaaa ttggagaatt   10620
agtaaaatgg caaatactat cgacctacgc ggtaacgaac agagcgttac ccgtgaagat   10680
gcggaagcgt atgcagcagc tttgggatgc actgcaatgt acttcgggtt cgatccagag   10740
cctaaagacg tggacccggc tatggctgta aagttcggac cgggaaaccc attctttact   10800
aaggatatgg agaagttctt gggaccggat gggagtcagt tcttttacaa cacggcgatg   10860
tatcaatgcc gtaagacgtg gagccttcgt gcttaccacg gagcacgcag cgtggagaag   10920
cttcttgtta atcttagtaa aggttctccg ctatcggtta tggcagcata cgttgactgc   10980
acgcgtatgc taggtctgtg tgaggaagcc cagatgagtg tattcatagc acgccagctt   11040
tgcatctgca atcgtgaccg taagcacgtg gaagaatgct tactgaaagc acaggagcac   11100
cagatgtcgt acatcgaaca cctaaaagcg aaagcttcct tgatgaggga ttagtaaaat   11160
ggaaagttca tttggttgga accgcgtatt actcgtaggc gggacaaacg cgggcacgtt   11220
```

```
catgggcgtg cttcgtgacc agcaggtgat acgtatggag aagaaagacc ccaacgtaca   11280
acgccttgga acacacgtcc tacaacgtga gcaagcccg gatgaaacat tcgataccga    11340
ggagtacgta gccacagacc acgccttacg agggactacg atctttgtac tgcgaggaat   11400
ggctggtgca gacatcccct gcgagatgtt gaagatcatc gctaagctgg atagtaagat   11460
tggtgagcta aattctagga tggagcttgc taatatagcc gcgatgaacg ttgctcacta   11520
cgtgaagaga gaccaataat atgcgtatga ccactatagc gtgtgcggtt aagatacact   11580
accgtgtccc ggtattgccg gagatgccga tccttatcgg gaataccaga gcattcgtgc   11640
agggtcgtgc tgctggtagt gggtttagta accgcgtcca ctacgacgtg tccatgccca   11700
agtttgtacg ctcagctgct acgcaagcat tcggacgcct tgaccgcgag tttaaggaag   11760
ccacaataga tcttacggat tatcaacatg cttggctgga ggtgagcccc aaatgagcgt   11820
agaagctgtt ttcgagcagg acatgcagtt agaccctgat atacgcaata gcaacgttgc   11880
aggggctttc tgcgtggcta aagcgaacct ttgcaacgcc tgtcagtggg acggtactat   11940
cgacgctact atgatggtcc tgttattcat gggcgttact aatttcgacg acgatctgat   12000
aaagcgttct gtcgagctgg gctactttag catcaaactc atgggtatgg ttgaccctat   12060
ccgtgtgaac cggggcgatg tgctcgtccg atcatctacg agcttcatgg tggtcactaa   12120
cgaagagtac aatcgcattt ttactaatat actgctatag gaggacacta tggctccctt   12180
cttcgttttc gcacagacag caaacacgat ggttaataca tgccgtcgtc tgggcatctc   12240
accaacagaa ccacgcctta tccgtgagcc ggagaactta aagggtgtga gctttcccaa   12300
ggtgggtgct aaatacatca tcttcgtctg cggcgagact gtaccactct ggctgcacca   12360
atttgctgtg ttaaataacg tattgctgct tggcatggac aagcacgtga tcgagtacta   12420
ccgtaagcac gacttccgag cggaagacta caacgcatac aataatagga ccgtatagtt   12480
tactgcaaca tccattttac taaaactaaa ggagctgaaa atggactcac gttacacatt   12540
tatcgaccta gttaaagacg tattcgcggc acttaaacgc gctaaagcca acggtgttac   12600
tttcaaaggt caatctccgt ccgctgtagc ggctgacatg gcgaagtacg acgctgacct   12660
agagagtgct ccggtagaag acttggaaaa ggctgtgggg cttgtgcaga gcattgacgg   12720
cacgtttaag tctggtatcg aagagaagct agactcaatc ctagcgccgt cggctgtgat   12780
catggactgc gacttcgacg acctgctaga agatacggaa gtggcttact gcgtcgatgc   12840
aaacctagac ctgctgacgg ttggtgcgta caatgccaaa ggcggttgct gcgagtgctg   12900
ccgcccttac taccgtgaat ccgtctacct actacgcgct atctgtatgc gtactggtga   12960
cgatattact aaaactgttc tggaccgcaa agcggctaag aaccaagttg gagacaagca   13020
ataatgcaag taccagttaa cattacaggt ccagtgggat cacttgccct agagtacatc   13080
ggcggtaacg ctgataaggt gattgagttc gttaagaact gcaccgggaa cactccgacg   13140
tttaaagagc ctgacgtgtt ggagtaccca gttatcggtg gtacgcagct gatcaccgtt   13200
ggcagttggt tggtgtggga taccactaaa ctgcactgca tggatgaagt ttactttagc   13260
aagaacttca cgatcatctg gaacatcca cagcagcctg tcccggtgga cgagccagaa   13320
ggtcgtgcaa taggctcata cgcgatcaac cactcgacta tcgctgaaga cttggacttc   13380
taccaccaca acgagtttgg cacgcgtaag gtacgctgta tcaagtcgaa ctacggtgct   13440
gaaggtcatc caatctacgg cttactaact ctagtttggc tagatggtga tgtgctatg    13500 tcgatgcctg ttggtgagtt gggagacaca gacgagttct caatggatta cctcggcgcg   13560
```

```
gtagaagctg ctaagcaggg acatcgcgtg tgtcgtaagg gttggaacgg cgctgacatg    13620
tgcctagtgt acgtaccagc ggcagacatc ccaacgaagg gaacaggtct taccccgttc    13680
ttcggtgata ccatgcctat gcgtgctcac tggttactaa aaaccgccac aggcgatgta    13740
gccagctggt ccccatcgac gtcggatagt ctagcgacgg actgggaaat ctactcacca    13800
gaataatttt actaaaatgt attgactata agaaacaggg ggaatatact tctccctgtt    13860
gtcgttttta ctaacccaaa aaggagttca acatggataa cgttatgcct caccctatgc    13920
caataaccta cagccgacct gagcatcaac gtcacgctat tcagtttact aaaaataatg    13980
ttggagcgtt gatccaagcc ctgatccacc tcgacatcgt agagaccttg ggtcttggtg    14040
aagaagcttc cgacgcgggc tttggtcgcc gtgagcgcgt tgttaagccg tgtcttttcag   14100 tggagcttag agattcgttc ttcgagcagt tcccacaccg tgcgaacacg tacgaggaaa    14160
atgagttctc tatctttgag ggggagtttc tggtgcttct aggcgctggt gatttcttag    14220
tgatgtcaga gcaggagttc aactcaacat acaagtgggg tcaggacgag cctgcgccgc    14280
tatcaccgtg tgtggctcca gagcaagatg acttagcgtc tattgccggg gaccgcgagt    14340
tctctgagcc tcgtgtagct gcgctggagc cagaggtggc tattgctgtg aagaggaga    14400 tggaagacct tgccgagccc attgaagagc cagaagagta cggcatcgaa gagcgagagg    14460
agtctcctcg tgcaaagcgt atggctaagc gtaatcgtcg tgactagcat tgctagtacg    14520
tttttactaa tctaataatc aggagaagag ttatggactc tacttacta acagtaacac    14580 cgaacaagcc cttccgtgcc gtgcagtaca acggtagtaa ctgggcgcag gtacgtcagt    14640
ttgctgctaa gtttgctaac gtagaaatcg cgatgaactt gaaagccgac agcccactgc    14700
ttgcgcacct tggcacaggc aatatactca tccctaaagg gaactacgta gttgcttggg    14760
gcaagtggga ccctgcgcacg tattcgccgg aagagtttac taaagtgttt gctggcattc    14820
cgtcaggacg tgaccaacta cttgaggtcg agatggacaa tgaccgtatc gtgatgtcta    14880
ttggtgtgga agccatgcgc atgagcatcg agtcgggtca ggcagacttc agcgtaggcg    14940
gcgcagtcca cgttgcagac gtagacatct ttgggcacga gctgatcagc tacttgaaag    15000
ctgaagctga agacggcggt actccagttc atcgcatgat cgatagcgta gcgttggaag    15060
cactagagca tggtgctcac ggtatcatcg agttggacga agaagactta gagcgagaca    15120
tctaatgggc gtagtaactg tacagcgaac caatccgatc atcgcgctcc agttcaccgg    15180
agataaccac gaagaggtga tcgagttcat gaagcaacgc ggtgggacca ccgtaacgat    15240
gcagtatgac aatttactaa aaattgaatc cgactgcttc ctatcatgga ctatccggca    15300
gggtgattgg attatccacg agaaagggtc cgtgtgtgag gtcatcttcg gagacttctt    15360
cccggatgcc ttccgcgttg tcgataacgg accactgttt ggtaagaagg tggtcatctc    15420
cggtactttc ggcaaggtaa ctcgccacgc tataaaagac ctcctatctg ctcgcggagc    15480
taaggtgttc ggcagtgtga acaagttcac cgacatattg gtgtgtggca aggacgcagg    15540
ctctaagctt accaaggcta aagagctggg aatccggatc atctacgagt cggagattct    15600
ggaactactc tagcacttt actaaaagcc tcctaacggg ggcttttttg tgtctgaagc    15660
attgacatgt gaaacagtgg gagtatactt cttagtaaaa ccaacgagga ttaacaaatg    15720
cgtattatct gtaaaatgtt cggtcacgac actccgtgga agactccgc gaatgtaagc    15780 cctatgtgga ctcctaagca agtctcccaa gacatcctgt ccggcgaagt ccgcgtcatc    15840
gacccaatct ataccgggta catgttccaa ggctacgagg gcgtgtgctc gcgctgtggt    15900
catactgtcc cggtatatgc tgataacgtg ccgatcattg agcctagcct agtgcctacc    15960
```

```
gacgacgaag agccactgga ccttaatcgt gaacaccgcc agttgtacct attctggtgt    16020
gatgttacta aaaagcacgc agatgcacgc ctataccta ctggtaagca gataaagtac    16080
ctatggcggt gtatctacaa aattactaaa gacaatcata acctgagtcc gacggagtcc    16140
gatacttgta actccatcgt gttctcatat tggagagcta agaagagagg taacaaatga    16200
aaaagttaat actggtgtta gcaatcacca cacttgccgg gtgtgcgtcc ccggaacgtc    16260
tacacaattt gaagtgtgac cagtgggtgt acgaacaagt tatggagcat ggggaggact    16320
acttcgatgc cgtgaaagag tgtggctaca aaaagatccc tatgtcggac ccactagacg    16380
gggcgtatcg tgtctacagc gttggggtg gttactaatg gaagccattt actacttcag    16440
cgactggcgt cattttgga tgtggcttga ctggaacttg tatgctaacg gcaatctatt    16500
cctgatgctc tgctggtctt ggatcttggc gtcgagccta atgggactcc gtgtcaagct    16560
ctggcaggcg ctctgtaaca tcctcgctgt atgccttacg tggatgttcg tttgttatgt    16620
agcctacgga accggactgg ggtgaaaaaa ttactaaaaa gtgtttgaca ctcatctgaa    16680
acaacgttac tatcctccct gttgaataca tttactaatc tactaactca gcagggagtt    16740
ttactaaaat ggctactatc actaatcttc aaaaagttat ccttcacgca gttgctacta    16800
tcaaagactg cacaggctac aacgtagctc accacttcat gcccgctaat gacctccact    16860
ggaccgcctc tcaccagcag gtataccgcg aactacgccg tatggagtct gcggacctag    16920
tggacagccg cgaagtccca caagacggca agcctaacaa gttcgtgtac acgctgaccg    16980
agaagggtaa gaaagcacat caagaagcta tcgcccacga gccatgcgac tacgctggtc    17040
ttaacaccca agctaccatc cacgcgctgt tcccaactgt agagtactac gcggcgtttt    17100
tgcagaagcg taacgaggag tgtgacgccc tgtacttccg caagtgtgaa gacggtgtgt    17160
ctaagctgga agagattctt attgaccgtc gaatcttgat cctacatgcc gagtgtacgt    17220
tcgcgcagaa gatgatcgta atgctgtctg agcagcagga agcgattgag ggcgaatctg    17280
aagaagtggt caagtagttt actaaactta aaggagcagg cgtcatgcgt ttcgagacta    17340
tcaatattta ccacaagtac gggaagtgga tcggcggtgg tcagctaagt agccgcagtt    17400
tggcggagct gctttccgct gcggtaaaac ctcaccaacg cgtggtctcg atggtttacc    17460
atgagaacca cggcatctca tccaactacg acatagtcct agaaaaccac ggggtgcagg    17520
tgctggacaa cgtgcatgag aaccacacgt actacgttaa caagtgcgct aaggactggc    17580
aggaggattc cctgttgaat ccagaagccg aggctacgca ggctaagcca gcatcacggt    17640
atcgtagaaa gtaactacta agccctcgca ctgccggggg cttttcgtta tactccaccg    17700
caaaaatcag gaggtaataa catggcttta tctaacgttt ttgacatctt gttcggaggt    17760
ggttttagta caccgggaaa cttcgtggct ggcgacgtgc tcgaccagat cgttgcctac    17820
accgaaccat cacgctcgga ggctggcagc acgctgacat cgctgtacac gaaatacca    17880 aacttcaaga cgacctgtag gacggagttg ccaaagcaca tgcgtgttac tagcagtgag    17940
atcaacacta tcttctcaca gttggacagc aattcagcag cgacactctc caccccttgct    18000 aatagtatcg cactgaagtg gcttgagcac gtaaacgaca gtagacaact ctaatccgta    18060
taattactaa aaacggagat taacaatgcg caaagaagta tcctgcttta gtaagagtgg    18120
aaagctcact aaagacatga aagttatttt agacatagcc accactatcg agttggcaat    18180
cgtaaacaat cctgacaaag accgaatcca agttattaag gaaacggctc gacgtcttaa    18240
gcaatcaccc cagtaccgaa agctgtgggc acagtcgatc ctaaacaagt acctgcacgc    18300
```

```
cgacgaaacc gtatccaagg cacagcagga cactatcgac agcctattct cgctccgggc    18360
ggctgggtac aaaacttact aaggagattg atgtgggagc acttcctaac aacaaccgca    18420
aggagtcgaa cgactctcca gacctttacg ttactaacca cccactggct attccgggtc    18480
tgttctcccg ctggcgtcca gagagcggtt ctatcatcct tgagccctgc tgcggacttt    18540
gccacatttc ggataagctg gaggagttcg gtcacgtagt acacagcttc gacatgttta    18600
actgggggcg tggtaacgct cgtgaagagt atgacgctca gtcgtaccat tacggtgagt    18660
atgagtgcat tattactaat ccaccctaca accgagctat gccaatcgta gagaacctac    18720
tggagcagaa tctggctaag ggtgggtcta tggctatgct ggtacgtctg gagtttcaga    18780
cggggaaggc acgagcggcg gctcttgagc agacccettt gaagtacatc ctaccgttcg    18840
cattccgtat cgagtgtgac aagggtgtag tcgtggagga gctggcggac ggctcttttg    18900
agacagagct ggagaaatcc ccgaactcat caaactacgc ttggtttgtc tgggaggatg    18960
gttacgaggg ctaccctact acgatgtaca tccaccaaga catggctgag caaacactgg    19020
cagaacttac taatagagag gtttagtaaa atggaaaata ttccggctaa gcagatagct    19080
gacgacatcg aagagctgtt ggagaacgct gctgtgtaca ttcagcgtca ggttaatccc    19140
atgctcttga agatgcgtac agggcagtgc atcgaccttt acggatttgt gatggatagg    19200
gactccacgg ctactttctt ccactgcaat gtacctgcgg aggagatacg cggtatttac    19260
gccagcacgg gcgaggtact gatccgtaaa gaagtaccgc taactcatgg tcgtttgtat    19320
ccgtcactgg ctctggctaa gaaccgtgct agtcaccgag tggctaaccg tattgagaag    19380
atgcgggcgt acagtcgatc actgtcaaca atcaccacga acgacgtcag caccatccaa    19440
gttaagtagc gtaccctacg atgcaagggc gtcacttctg cccttgcatt gtgctaaaga    19500
gttgaacgct gtgtacaacc gcaagagtga cctttttagt tagacgtata tttgtatgaa    19560 ccatttttact aagagtaagg gagatgagaa gacgagagag aagaacggct gatcagcctg    19620
ccattatgtg ggaatgggaa gacctaaagg acaaccctaa taaagtcgta tccgcactac    19680
ttacaagctc gtacctgtat tacctgcgcg gcgacttacg tcccataatg cgagacgaag    19740
actttgacct atgctgcaaa ttactaagac gtagataccg tgaagtaacg cacatgcaca    19800
agtccttgat caagatgtcc gacctacgcg ccggaacctt gtttagactc cgggaccacg    19860
attcccaaac catcacgaag gtggtggctg tagaattgtc tctggggacg attaacgaca    19920
tgaggctacc aacgcctcaa cccgccgtta aaaacgccac cacgagccgg agaactcgaa    19980
ataaagctgc tcctaggcgg gagcgtagtc gcaagaaggg gttttttataa gatgactgtc    20040 accgggacgc taattatcct actcctcatg atggaggcgc tatcgtgggg attctgggta    20100
ctatggcgta agttagtaaa atcaggacgc attcctacca tcaagtttaa taagcgccga    20160
cactggtgtg accttaagta cgtctacacg cgtgctgagt ggcgggggca taggaccccg    20220
ttcgtatggg ttactgagcg ggagtatccg ataccagagt ttactaagaa ccacccggac    20280
gagctggcga cagctgcggt tcgggacttt gttgcccagc tcataaacga tagtgagttc    20340
gtactagatg ccaccgataa agaggagatg ttctcgcagt acagtatctg gcttactaaa    20400
catgcaatgc cggacaacgg ctacgcgatc atagaagact ggcgagacca gctaaaccca    20460
gcgaaggatg gaattgacga tgaataacga taaagtgaag gaattactaa ttgagcagta    20520
cggggcgcta ttagaggagc caacagattt ctttatacag cctagagatg atgagttctt    20580
cttcgagcta aacaacacta aggcgtattc aatccgtaac ccgtgggatg cgagccagcc    20640
gaaggtccct acggtggaca cctgcgttac cgctttcggt gagctgtgcg cagctgctgg    20700
```

```
cattttccta aacgaaacgg tgcagtgtac ggaatttgtg ggagacggta ctggtaagtt    20760
cgatttccta aaaatcccag tgcgcgggt  gatcgtggct atcacggtta tcgaagctcc    20820
atcctcgctt ggggctgtgc aagttatcgg tcagactgcg gatcgttgct ttgctctggt    20880
tacggtctac cgcgaagact cacagataaa tagtcagggc aatgagttca tcgctcagac    20940
tatgaatctg aagactggca aagtacacac atgcctgttc cgtctagctg tcgctgaaga    21000
ccaagacacg ttcccagtgt acgttccgaa gatggtgtca gtgaatggct actacaacgc    21060
gcaggaagcc gttgacaacc aagctgaaga cgttaagaat atggtcccag tggctgactt    21120
tactgagtag gtcactaggc gaaccggact tccttcggga aaccaaagcc ctcacatcta    21180
gcggtgtggg ggctttttt  gtatcctacg gctgacaatt tacttaacga ggactgcgta    21240
tggcagacat aaaggagggc gtgcgttcga aactagacct atatgaagtg cagctagggc    21300
gctgctttta ctgctgtaaa ccgatgtctc cgggctctta ccaaccgagc gtccgtgcca    21360
acggctttac tagggaccac tttataccga agtgtgaggg tgttcccgga tttcacaata    21420
ttgttttaag ttgtaagtac tgcaacgaga agaaggcaga caaggagcct tcaaataagg    21480
ctctggctaa atacgagtta ttactaagag taagggctgt gttccctgac cataatcaca    21540
aagactcggt acggctttct cgttggaaga ttaagtactt ttaagtttag taaaggagac    21600
tatatgagtt tctggcgtaa agaagagcca gtgatgacg  agaacggcaa actgatcaaa    21660
ggcggtatgt ttgcccacca acgcgagttt tgggaatcag agagtttcat taccgcgtta    21720
gtaaccgggt acggtggtgg gaagacccttt accgcaggca agatcagtat ctcaatggca    21780
ctggagaatc ccggcatacc gtttatgtgt gtgtcgccgt cgtacaaggt cgctcgtaag    21840
acgatggtaa ttactatcaa ggaactgctg caaggtaagc agtctttgct agagggtttt    21900
agttggaagt acaacaaggc ggactgggag ttcttgatcc gatacaaagg tcgtgagggt    21960
attatctgga tcggctcagg cgatgacccg gacgccctta aaggtcctaa cttgtgtggg    22020
gctctgattg acgaaccgtt catccaatca cgcgaagtat tcgagcagat gcttgctcgt    22080
gtccgtcacc ctaacgcccg cactaaacgg atcatgctga caggcacccc ggaggacttg    22140
aactggggat acgacatcac tgagggtgag gagaaggaga acttcgacgt acacttggtg    22200
caggcatctt cgaaagaaaa caaagcactt ggtaaggagt acacggaacg ccttgagcgt    22260
ggtcttagtg ctcaggctgc tgagtcgtac gttagtggta agttcgtacc gctggctaag    22320
ggtcgtgttt actacggctt cactcgtgag cgtaacgtta tggagttccc ggagattcct    22380
aaaggagcta agattggatt tggtctcgac tttaacgtta acccgatgtc ggcggctatg    22440
ttctggtctt tgaatggaca catccacttc tttgacgaga tcttactacc gaactcggac    22500
acctacgaca tgtgtgagac aatattggct gagtatggac agtaccgccc tatctgttac    22560
ccggatgcta ctgggcgtaa gcgtcagact aacgccgctg gcggtatgac cgacttccgt    22620
ataattaggg atgagtacaa gatcaagatt gacgttggtt ctaccaaccc gcctaagcgt    22680
gaccgataca acatagtaaa tggcaagctg aatcctaaga agggcttgcc tactatgact    22740
atctcaccga agtgcgtgaa gatgatccgt tacttagagt cgtactcaca cgagaaaatg    22800
aagcaacaag aagagatgtc ccacatcttg gatgctatgg gctaccctgt agcgaggatg    22860
ttcccgctac acatgcgtgc gggcgttact aaacttgcag gtcactaagg agattttact    22920
aatggctgaa gaaaacaaga aggctgagaa agttacattc acagctaaag agattgagca    22980
caagaataag atttacaccc agaagattaa acgctgggag aagaaccgcc tagtgtgtgc    23040
```

```
tggtacagac gctgtgaagg aggctggcgt taagctgttg cctcagttgg aaggtcagtc   23100
aaccgacgag tacgatgcta tggtagttcg tgctaacttc ttccccggag ctctgcgtgc   23160
cctgcacggt actaacggta tgatccacgc caagactcca accatcacgt tcccggaagg   23220
taagatgtct tatttagata acatcggtct atcgggctca tctatcgcgg aagtggcaga   23280
ggaaattacc gaggagcaga tgctccaagg ctgggtaggt atctttgcgt tctacaactc   23340
cgttccgggt acaagcgagc taagccgtt cctatcagta atccgcgccg agaacatctg   23400
ggactggcgc ttcggtgtgg taaatggcgt taagcaacta acgtacgtca agttcgttga   23460
atacgtcgag tcccctgact ccaacatgtt cctatccgtt gagatcccgc aagtaactca   23520
gctgtggtta gacaagaatg gtaagctgaa ctaccgcatt gtgcagaagc aaccgggcga   23580
gcagaagggt gaagcttcat gggtccaaaa acagggcggt gcagttttag taaggggtaa   23640
ggaagtcgag ggagttcctt tccgtttgat cggtgctcgt aagatgtcgg gtcgtccaga   23700
ggaagctcct attgagccta tcgtagacgt caacatctca cactacatca cctccgccga   23760
cttggagcag ggtcgccact ttaccgcact gccaacaccg tacatctgtt ccgcatcgtt   23820
agacccagac aaggacttcc gcatcggtgg ttacaactgc tggatcatcc cggagaacga   23880
agccaaggtc ggtatgcttg agtacaccgg gcaaggtctg ctttcactgg agaaagccga   23940
tactgagaag aaatgggaaa tggcagtact gggtgctcgt atgctccaga acgacaagaa   24000
agccaatgag tctaaagaca cggtccgact acgtcagacg ggtgagaaca gtatcgttac   24060
taacgtcgca cgccagtgtt ccgtagcact aacctacctc cttggtaaat tcattgcccc   24120
gtggaccctc gtctctagtg gtactaaagt aggcttcgta ctaaccacag acttcttgac   24180
catcgagatc tcaaccgaga tgctgaactc aatggctgcg ttggtggcta ccgacaagat   24240
gtctatggaa acattcttct acaacttgca gcgtggtggt atctacgaag cgggcactac   24300
tcttgagaaa gagatgcagc gtatcgagaa gcagtttgaa aagcagatga gcaacttgg   24360 tcgtaagagt gacgtggtgg acttagacga tgaagaagac gagatcccgg acgatgagca   24420
ggctaagaag gacgagaaga agactgcgac taatgaccac gtagacaatc aagctaagag   24480
taaggattag taaatggcga actttagtga caatctggcg gtagtttacg cagaccacca   24540
gattgaccta taccgctatg aagccaacca gcggcaagac attgccgctt tcctactggc   24600
aatggcggac gagataagag aggcgttact aaaagctgac ttcggctcac agccgttgt   24660 tactaaacgt aaactcaatg cgttactaaa agaaatcgaa gcaatcatca agcagtacta   24720
caaagacgct cgtgactacc agctaggcga gctgaagcag ttaagcgtaa tcgaatacgc   24780
ttgggctatg tctgcgatga caacaccat tggtgccagc ctgttcgaga ccttccttac   24840
taatcacttc ctagagagtg tcgttagtaa tgtcctgatt gaaggtgctc cgtctaaaga   24900
gtggtgggct cgtcaggcta cagacacaat ggagaaattt gtagaccaga tacgtatggg   24960
tgtagcactc ggtgagacta acgaccagtt aatcgaacgg gtgaacggca gttcctcca   25020 taagttcggc aagcgtaaga tgtctgatgg taaggttaaa cgctacggct tgtacgaggg   25080
tggaatactc aagacatcgc gctctaacgc tgagacttta gtaagaagtt ccgtgcaggc   25140
tattgcgaat gatgctaaga tgcgaatgta cgcagctaac gacgacctac tgcatggtta   25200
tcaacagcta tcggtactgg acttaaaaac atctgacatc tgtatcgccc gaagtggtct   25260
tgcgtggacg gtagagggta agccgattgg gaatcacaag aagcgtttcc gaatccctcc   25320
tctacactgg aattgccgat cactactgtt accgattctg aaatcgtggc aagatatgcc   25380
gggtaaagtg cgtactagcc ttccgggaag tatgcaagcg agtatggatg gtttagttag   25440
```

```
tgctgaccag acgtacgaag atatgctcaa gcgtcgtaca gatgctgaga tcaagaagaa   25500
gcttggaccg ggtagattcg agttgtggaa acagggtaaa ctaacactac gtgatctcac   25560
cgaccaagat gatcgaccat taacattgaa agagtatcga gaaagtgctt aaaatacacc   25620
tcgattttac taacagtaac atgaaggaca aaacaccatg cttaaattcc gtgttcagaa   25680
actagacgac gtgaaagaag agttccgcca cctatacatc caacaagctg acggctcttt   25740
ccaactgggt gtagaaggtg cggtggacaa agcgaaggta gacgagttcc gcaactctaa   25800
taccaacctg caaacagcta agaacagct tgagcagcaa ctccaacaaa tggctactaa   25860
gttcgacggt ttagacccag agcaggctaa agaagctatg gagatgatga acaagatccg   25920
cgaccagaag ctaatcgaag aaggtaaaat cgaagagctt atcgaagcgc gtactaaaga   25980
catgcttact aaccaccaga cgcgtgagca agagcttacg aaatccatta aggactggga   26040
aggtaagttt agcggtcttc agtcaaacta ccgtaagcta aagatcggct cggacatcct   26100
tggtcagcta gacaagattg gtaaggttca cagctcatct cgtgacatca ttaccgacct   26160
agctgctcag gtttggcaat tgaacgagaa ggacgagctt gtggcaatga aaggcgacca   26220
gcctgcatac agcccagccg acgctactaa accactatca gctgaagagt ggtgtatgca   26280
gctagcgaat gaccgtccgt acctgtttga gtcaactacc tcgatcagtt ctggtcaagg   26340
tggtcaaggt ggtcagggcg ttaagggtgt tatcagcggc gacgatatgg acgcattcga   26400
gaacaacctt gaagcaattg catccggtga agttcaagta acgtctaac tctgaatttt   26460 aattttagta aacataaagc caccttcggg tggcttttta gttttattta ataagggggt   26520
tgacgaactt agttgtttgg gttttataat gtaaccaaca aaagcaaact tgtttagcgg   26580
cggggtcgct tctcaagggt ttcggggaaa ccatgcgaaa gaacttatca acgacaaca   26640 cgaggactta gcactatggc taatacttta gaagctgtcg ccccgaagct gttagctcag   26700
ggcttaatgg cacttcgtgg cacgaacgta atgccgactt tagtaaaccg cgattatgat   26760
cgtgatcttg cagccaaggg tctgacagtg gatattccaa tcccttcagc ggttcctact   26820
caggacgttg caccgggcgc aacacctcct aacactggcg acgtagcgcc aacagtagcg   26880
aaagttacac tagacaagtg gaaagaagca cctttctacc taacggataa agacgttaag   26940
caatcaatga acgtatcat cccgcttcaa gcgtctgaag ctgttaagtc tcttgtaaac   27000
gacgttaacg cggacatcct aggcaaatac acttctgtat acggcatggt aggtactccg   27060
ggcgtaactc cattcggttc aaacaccaaa gaagcaactg acgctcgtac taagctgaac   27120
atccagcttg caccgggtca agatcgtcgt ttcgttatgg acccatctgc ggaaggtaat   27180
gcacttaacc tacgcgcatt caacgacact aacttcgctg tgactgctca gcaagtacgt   27240
gacggtaaaa tggctcgtaa actaggcttc gattgggcga tggatcaaca agtacctgtt   27300
cacgctgctg gtctttcggc tgcggctgtt aacggtgctg gtcaaacagg caaccaatta   27360
gccttcgacg gtgtagagta gctgctgac ggtggtactg gtgttaaagc tggtgacatc   27420
ttcactattg caggtgacgc tcagacttac gcagttgtag caactactgg cgctaaagct   27480
ggcactatga ccgtgactcc ggcgatcaag aaagctccgg cggacgacgc tgtgatcacg   27540
ttcaaagcta ctcacactgt taacttggca ttccaccgtg acgcgtttgc attcgcatct   27600
cgtcctctgg ctgaccaaac taacggcttg gcaacatca tccgtactgc aactgacccg   27660
gtaactggtc tagcactacg tcttgaaatc agccgtgagc acaaacgtac tcgtttctcg   27720
tacgacctac tatggggttc atctctagta cgtccagaac tggcagtgcg tgtagcgggc   27780
```

```
taatcccgta taggtcatgg gaggtagggt tatcccgcct ccctattttt ttaagtttag   27840
taaactgaga gtacgaatta tgagtcaaat tgacccgcaa gagatgctta agcaaatctt   27900
agctgcatct gataacccag cagaactact acgtggtgcg atccaagaag ctacaagcgg   27960
tgagaacggc ggcaacgctc ttcaacagct tgaattactt ctagcatctg accctaacct   28020
aaaacaccac ctacgctctg gtatgcctgc atccgtgcaa gaacacctac gttacgtacc   28080
tacattgatt gttacgttta ctaatggtgc tttcggcggc aaaccaatgg tgatcaacaa   28140
gtcggacttc gacgctgacc ttcacgaaga agttgacgtt gctaaagctg ttaaagcggc   28200
tgctgcttct gctgctaagc aagaagagcc tgtcgtcgat gaaggcgctg gcgaagacgc   28260
tacaggcgaa acggaagatc agaccgaaga cgctcctaag cagggtcgta gccgtaaccg   28320
ccgtagctaa ttagtaatac ctattactaa cgttactgtt gattggaagg aggaggctta   28380
ggcttcctct ttttttgtttc tggagattac taaaatggca atcacattaa ccgtacagac   28440
tggaatctac ccggtacgca atgccaacgc gttcgcgtct gtagagcagg ctgacaatta   28500
ccatgcgcag cgtggtaata cagagtgggc aggcttcgac gccgacaaga agaaagctgc   28560
actgatcaag ggtgcagact tcatcgctca agagttcaat ttccgtggtc gtccgatgta   28620
tagcgaagaa gacccgacta acccacagtt cctaccgttc ccccgccatg acttcgtaga   28680
caaggctggt cgttctatta ctggcacgcc ggaaggcgtt gttcgtgcta acatggagct   28740
ggcattgttt gccggacgtg gggacctta ccctaaccag accacattac taaaaccggg   28800
tggtgctgtg actaaggtta gtaagaagac gggtccattg actactacgt acgagtacgc   28860
aaaccctgta gccgttctgc actcaacacc acactacaag aaggtgagca gctggcttaa   28920
ggactacgta tacactaccg ggcgtattca ccgatagggg attactaaaa tggctaacgc   28980
ataccaagag cagatcgacg acgctctgga agtatcaag gaagcaggca agcagttcga   29040
cttcgcgctt actactgtgg gcaacaaccc ggataagccg tggctaggtg gtacaaccac   29100
cacaaccgat gtcaagctgt gggcttgtgt ctttccggtt agcagtgctc cttctgcact   29160
acgtgagccg atgctcaaac agggcaccat gatcgaaact caaatgcgct acgtgctagc   29220
agctggtgaa ggcagaacta cacacccaaa cacaggtgac gtgctaaagt catttgaggg   29280
gaacgactgg gcaatcatgg catgtgcgcc tcttaccgtt aacggggagg ctgcgatcat   29340
ttacgagatg gtagttaaac gatgaacgac atagaagcac gagaacgcat taaccaagaa   29400
cttactaacg gctgggcgac ccattctgcc acggttgata ttgcctacga gggcgatggt   29460
tacaagccac aaccgggcaa ggcttatatc gaagttattt tcagtgtaga atccacttca   29520
agccagtcgc tgggtgatga gggtaatcgc tcctttatcc gcgatggtgt tgtacacgtc   29580
aacgtgtaca ctccggctaa caacggcaac gccttcgcag ctcacatcta cgctatggct   29640
gtacgtgata ttttcgaagg taagcatttc ggggaccttt ggttctggga gtgtaaagca   29700
agtcctgccg ggaacgatgg gacatacaac gtagcgtacg caaattgtgc gttccgcttt   29760
cagcaaatca gtaggagaa ttactaatga gtgatactaa ccgcgtacgt cttgccattg   29820
tggaagagac tacaccgggg actgtcccta acaaccctaa gttggtacgc cagcgcgtta   29880
ctaacatgcc gtctctagcg gtaacgccgg agactatcga atcggaagaa ctggacccgt   29940
ccatgcagac aaccgacctc atcaaagtag gtcaggctgt tggtggtgag ttcggtatgg   30000
agttcagcta cgacgctcag aagcaatcaa tggtcggcat catgcgtaac agctggaact   30060
cgttcacgca gtacaagggt gatgaagttg gcgctatctc agctggcaaa gttgctgtta   30120
ctaacgtagg cgctgcgcta cctgttggtg cgctggttct gttcaagaac ttcaacaact   30180
```

```
ctgataacaa cggtgttaag cctgttacgg ctgcgaccac cacagatatt acagctacgg    30240
gcttagtagc cgacgcgtct aagacgggta aggaagccat tcacgtagtt ggtctgcaag    30300
gtggctctgg tcatctgact gtcaccgcaa acacgcttga agctacgtca gggtcgaaca    30360
tcgactttac taactttaag ctacgtccgg gctccttgat caagctgggt ggtaaggacg    30420
cggctaaccg cttcgctacg gctaacgtga acgctatggt gcgtgttact aagattgaag    30480
ccaagaagct tacgttatct gacctaccta ctggctgggc tgctgacaac ggtgctggta    30540
aaactattca agtctggttg ccagaggacg acattgtgaa cggcgtggct accaagtcat    30600
tcacgttcct tcaatcgttc ttggaccaca acccggtaac gcaccagatc ttcaatggta    30660
tgcgtatcgg tactatgaac atggagatgc gttctaagca gatcgttacg ttcagcatca    30720
acgctcaggg tactaagggt gctatcgacg agacgggtgt ggcgggtgct actatcctgc    30780
cagcgtctac agacgtggta atcaacaccc cgtctaacgt tgcggagcta cgcgaagctg    30840
gtcgtaagat tgaaggtccg aactacgtga caggcgttac actggcgctg aacaacaacc    30900
cacgtaacga cgacgcaatc ggctacgagt ctccggttaa catcggtggt ggtacgttcc    30960
agctgacagg cacgctaaac acgtactttg gcaacaagtc gctagttgag aaggtgatca    31020
acaactcgac aacgtcactg ctcctaaact tcaaagacgg tgaaggtcag cacgtggtgt    31080
tcgatatgcc acgcgttaag tactctagcg gctctccggc ggtatcaggc aagaacgcgg    31140
ctaataccgc agaccttggc tacacggctc tgaaacacct agactacggc tacacgctag    31200
gcattcagaa gttccgttac atggagtaaa tcgaagcact tgcgtcgagg cacaacctag    31260
aataagatca aagcgtccaa tacgggcgct ttttaatat tagtaaacaa ggaaatccca     31320
tgaagaagac taccccttc gctctattcc gcacctctac taacgacgaa gtgaacggcg    31380
tagtggtaaa ctacggctca ttccgcgtta cagtggcgta cgctggcggc gctaacacag    31440
actacaaccg tctgcttatg aaacttggta agccgtactt gaaactaata agtcaggca    31500 acctgccaga agaagttacg aaagagatcg atgagaagct ttacacgcag accatcatca    31560
agaactttga agtagacgta gctgaagaag gtgcagaagc tccagtgtgg aaacgcggca    31620
ttccaactga agaaggtgaa gtcctagact acaacgaaga gaacttagta agcctactac    31680
gctcccttcc acacctattc gaagacatta agtcattcgc tcaggatatg tcgaactaca    31740
aacctgatct ggaagtagct aagggaaact aatagagttt ctaaagcatg agctggaata    31800
cggggacgat gatttcacgt ttatcattga agccgcaatc gaagccggag acccacttcc    31860
ggcttttgct tcagaagcgc cgaaactcct agacccatta gtaccaacct ataacatgtt    31920
ctgggatata taccgataca gacgtgttat cgccagaaat gattttgtcc cttgggaagt    31980
ccttgaacgt ttcgccgcta agtacgggat tgaagagctg ggagagtttc aagagttctg    32040
tgagttgttc cgcgagatgg agaaagttta cttagaccac ctagtagaac agtacgaaca    32100
ggaacagaag caggaccaga atcaacaagg gggacagcat ggcgaatttc tcggacatac    32160
ctaaagatct aaagcacttc gctttcaccc tccaagctaa taccgaaaca aggcagcgtg    32220
aagttgcctt gaccattacc agagagctta tgcagcgaaa ccctaagaag acgggtcgtt    32280
ctgctggcaa ctggcaggtc ggtatgaatc gccccaaact aattgcacag gctcctccgg    32340
tagcggagag ggcttcggat gaagaactta gtaaaagttc taaactgttc gtgcagaaac    32400
aacttagtaa agcgattaac gatattacta agggaactct acgcggggat gacccggtaa    32460
tctatattag taataccatc aactatgtag tttacctaaa caccacccga ccatcaccac    32520
```

```
aggctgctcc gggctggatt gaagcatcga tccgatttgg cgcagatagc actaagggag   32580
tgaaacttac gtaatggctg gtgaaagtta cattatcaag gtacggcaac acggtgcgcg   32640
ggaggtcaaa cgatcactcg attacatcgg tgctagtgct aaacagacca cgagcacact   32700
ggagggnatg cgcaagggct tgaacctcct actgggtctc tacggtctaa cagcactaca   32760
gcagtatgcc gacgaatatc aaaacttgga tgcgaagctt aagatcgcaa cgcatagtac   32820
agaggagctg gctcgtgcag aggaccagct tttccgcatt gcgaacagaa cgtattcctc   32880
attctcaagt accgttgacc tatacgcacg ttttgagcgt tctacacgga gtcttaagat   32940
ctcgcaggat aacctcctac agatcacaga gacggtgaac aaagccattg ccttatccgg   33000
tgcaagtact caggctgcta acgcggctat cttgcagtta ggtcagggta tggcggcagg   33060
cacactccgt ggtgacgaac ttaactcagt gctcgaacaa gcaccacgtc tagccgaggc   33120
aattgcttcc ggtatgggcg ttgctgttgg taacttgaag cgtcttggtg agcagggact   33180
tatcacaacg gaagaagtac tcaacgcact tgcgtctcag ggtgctgcta tcgacaagga   33240
gttcctaaac gtaaacctta ctattggtaa agcaatggag gttctgaata accagatcct   33300
acgtgccatt ggtcagctag atagtaagct aggcatctcg tctaccatcg ctaagtctat   33360
tgtaacgttg agccaaaacc tcgaccaagt tgcaggcgcg gctcttggag ctgctgctgg   33420
tcttgcagta atgtacgctc cagcattact aaaaggatta gtaactgtta caagattagt   33480
aaaaggtctg actctggcta tggtttctaa cccatttggt gcgattgcag tagctgctgc   33540
caccnttatc ggttatttga ccgtcatggg cgaccagatt aagcctctga gcgatagttt   33600
cgctactgtg gctgactttg ctactgctgg cttcgatatg gcgtcagaat cgctctcagg   33660
gctttatagc ttaattgagg atgatgtcaa ctctgctctt agcaccatgc gtaccaccgc   33720
agacgaacta tttactaaga tgggaccgtt aatagaccaa gcaatgtcta tcggttacga   33780
agctatcaac aaagtgatcg gggcgtttgt tattgctcgt aaggtcggcg ctcagctatt   33840
cgagctggta ctacagggtg cttccggtct atgggaaggt ctaacggcat tctacgactt   33900
ctctgtaggt ttggctaagt cgatgttcca gactgtcggc ggtattgcca acacggtatc   33960
gaagaacact ggcattactc tggaatcgct ggctcaagga ttcaagcagg ttcttaacat   34020
cgctatcggt gtgttcacgt taattccgcg cctagcgttt actatggcga gaacgtagc    34080 gaagaacttc gaggcactgt ttgcagatat tactaatatg ggctcggcta caatggaggc   34140
tctaaaagta gcgttctcag gcggtgactt tactgaagcg ttcaacaaga tccgagctca   34200
gtccaacggt gcgatggacg gtatgggtga cgacatatct ggcgttctaa aggacacgtt   34260
caatcaagac tacgttggcg accttattgc taagactgtc gagttgaaag agcagttcat   34320
ggacacgttc ggagatgacc ttgctcaaga ctacctgagt gacgctcagc aatctctaag   34380
cgagttctac aaggagttca agacacgtgc tgaagatgca gctactgcac gcctagcggc   34440
tgagcaggaa gttactaaag agtacgagaa gcagaacaag attgtaggcg gtggggatgc   34500
tttcagttct gaccagattg ataagtttac taagaagctt aacgctatgc gtgagactct   34560
taacggactc gacccaactt gggaacgctc aactgagatc atcaacatct ggcgtgatac   34620
agcccttaac gcggtagaca agaactggga gcgttacgaa gagtacgcga acatggttga   34680
ggaagttaca cgcgagaaga tcaacaaagc ctactgggag cacatggacc aatctgaggc   34740
tgctttcgat ggtatgatct cagccgcgca taaaatgcag aaggagtacg acaactctgc   34800
tgaactcatg aagaaaggca tgggcacggt gattgacggt cttactaacc agttcatgcg   34860
atttgctatg actggtaagt ttagcttcaa agagctggct gctggtgttg ctgcttctat   34920
```

```
cgctgagatg atgatgcgta tgctcgtcat gcgggcggtt ctggcggcgt tgaacgtcat   34980
tccgggcttt gctgctgcta tggctggtgc tgacgttgct ggtcaggcgg caaccgctgg   35040
cggtgccgct gctaacttcg ccacatccac ggctgtacta cagcaaggta tggggcaggc   35100
gcaggcggct aactctaaga tgtatgctaa gggcggtgct ttcagtcgag gtgttgagat   35160
gtttgctaac ggggctgcgt ttactaacag cgtggtatct cgacctacaa acttcgcaat   35220
ggctggcggt cttggtatga tgggtgaagc gggaccagag gctatcatgc cactcacacg   35280
aggtgcagat ggtaagctgg gcgtagaagc cagtggatcg gctgctccag aggtaaacgt   35340
gtacttcgta cagagcgccg atgaagctgc ggaactaatg gcacaaaacc cgaaagctat   35400
taacaaatta gtaagagcta tggaagaggt aaaaggttaa aaatggcata tcaaacggga   35460
acagctacag gtcataaaga cctgcttgct aagctaagaa cgtttgctac agctaatggt   35520
tggacttctg agcagtggtc caaccccgct agtggcgagc atgaactggt actaaaatcg   35580
acgggtgtcg gtggtgacga ttctatctgt gttggatacc gtacggttag taacaccgcc   35640
tcggactatt ttaactggga cctgtggact ggtcctactt acacaggtgg ggacttctgg   35700
tcgcaggctg ggcaatcacc aagaaggtgt ttgttgctct ggggcaatag cattccttac   35760
tggtttgtag ttactaagcg tagcatcgtt gtcgtggcta acgtcagcac cacttatcac   35820
gtatcataca atgggctgat aaccacgtac acttcacggg gtcactgggt ttccccacta   35880
gctagtggtg cttctagcag cgtaaacacc ttacgttggt cagacacctc agacaacgtt   35940
ggtggaatac agaaggttaa tgggagcgcc accattacgg ttcgtgataa ggatggtaac   36000
tgggcaaacg tacacactat gtacccacac tctgggggag gtcctatttt actaaacgga   36060
tacgcctctg gtaataaggc agtacagcaa tacatctact ttgcgtcaga ccgggtactg   36120
ggggagcctg ataacctatt ctacgtcaat ggagctacgc tacaagcagg gcagacgctt   36180
gacaatgccc aagtaacttt tgtatgtatc ccgaacatat tcagatctgg ggtgcaggac   36240
ttttacgcag tgaggttagt ataatgccat tttactcttt aacgggggtt gacactcctg   36300
agaaagtatt tgccgctatt aaggaaaagt tagagttgca cggttataca aacgtgacag   36360
ctacagcatc ctcaatactg ttcgagggac ctgccactgt agtaggtcag cgttggagcg   36420 ggtactttc gctgggcagg cagggtagtc ggcaagcgta ctataccagt atgtccgtcg   36480
gtgagggtgt taatgggact tctcacataa acgggtctgg taatgctacg ccagtgaaca   36540
acggcaacta caataggcag acagaccacg atatatacat aaactctggg accaccctcc   36600
agctctttat cactaagcga gctatgcttg ttcgtgtagt gggcagggat gcaaactacc   36660
ctaccagtga tgctagcatg gtacttatat tattcgccct cggcactaca actggggagt   36720
ttggcagcaa ggaatttata ctgtgctctg gtccgcagag taagatcact agccgctggt   36780
atacttctac ggcacttggg acaccatatc gcagctacaa tggcggtgct ccagagacga   36840
atacaatgct acttaagtac gacgcagcgg gcgttaaaag ctgggttagt agtaggtcct   36900
ccgagaatgg cttctacggt aagccgggag acgctaactc gaaggacgc tacatgggaa   36960 tacttagtaa gatgaagttt ccggacagcc ttaccaccgt aatgatgcct atgtacatac   37020
gctcaggcgg tgagctttac ggagagctag acagtatgcg ggctataccg atgtcttact   37080
acaacaccgg ggcgtcgttc acactaaact cgaagaagtg gctggtgtgt agtacgtcgg   37140
agtggaagca agacgacagc tcacacttgg gctttgcaat gttggaggaa taaatggcag   37200
acggatactt actaactggg gctctgtggt cccagctact cccagaccct ccagtaccaa   37260
```

```
caccacaacc gctgtatgac ggtggtgggc acctcaccta cgcttctccg gggtcggtac    37320
gaccccgtga gcagacccct acagggagga gcgcctacgc tcgtttagga ttctgggagg    37380
acttcaaaaa tacgctgttc ctacaaccgt cggtaattga ccttggggcg atcctaaccg    37440
cgagtacgca cagcatacgc atctggtcgt cgtacgaatc taagatcacc gcccctcta    37500 taacgcgtgt ggggaccacg gggctagaac ttattgggcg taccactaac gttgctctgg    37560
cggatcgcgg gggttactca gactacaccc tgaacgttac tatgggtgtt tctggcgtcc    37620
tcgatgctaa attcacatgg gaatttccgg gaatagccac ggctctaaaa accctaagtg    37680
tcacgggcac tcgggtgatc gtatacgacc caccaccaca gaagcgggta acggaacgac    37740
tttcatggca tactgctgtg atcaaaacta tggactcgaa ggaacaacga attcgcctta    37800
agacgtaccc agcagtggaa gttacctaca ggtctcttac taatattaaa gactcttcta    37860
agtacgaggc gatgcttttt ggtctagggc acggcgctct ggcagtaccc gtatggcacg    37920
aggcagtgcg atacatcggg tcgctgccta tcggcactac tgctattagc ctcgacacac    37980
gcggcagtaa cttttagta ggagaacgtc tggtgttgtg ggcaggtatg gggcagtacg    38040
agacggcaga ggtagagtca gtaactgata ctaaaatagt cttaaagtcg gcgttactaa    38100
agtcgtggga ttctccgcta gtggcaccaa tgttctacgg caacgttgac cggagtgact    38160
ttaataaata tagggtagct gctgtagata gtgttgtaac ctatacacgc actacgacag    38220
agttgacggc ggaagcccag ccctacccag tattcgatgg actgccgatc ctgacgggca    38280
agctgcatac gtttagtaag actagcccgg tgtctatatc ccatgatgta actcagctac    38340
agcttgggtt tacaccacct aaaaacgtcc agcagtttac gttccccaat gttagtcgcg    38400
acgtggatgt ggttctcagc agtcagcgcg aggtccgtga cttcaagaag tggttaggct    38460
atctgggtgg taagcagcgt ccgttctggt acaggtcggg tcgtaaggag atcgtcgtat    38520
atggtacgtc tctacaggac actgatactc ttaccatcga ggacatcgga ttcgcggagc    38580
actacgtagt atctcccaca cgtaagtgga tcgcggtaca gcgatcaagc gaccttacat    38640
gggagtacta cgagattcag agtgttacga aggtagaccc tacggtgagt gaccccgcgt    38700
tagaacgtct taagctaacg cgaaacctgc cttacgcaca tacgtcagag tcagtaaata    38760
tggtatgctt aatgtccccg gtacgtctgg actcagacca agttactatt gtgtgggaca    38820
accttaatca tgccaagtgc tcacttaaag ttttggaggt tagtaaataa tgagcttcac    38880
tgataaagag gacagcctct atgatggtcg ccccgttacg gtgtaccagt tcacgattgg    38940
ggagaccaat tacgtgtata cctcctcaga tcgtgacatt aactcatcgg ttggtctcgc    39000
taaagcggta cacataaaac acggtactat caaggagacc actgaggata agaggtcaac    39060
cgttaagatt gagttagacg ccgacacggg tctagcgaag gcactgcgcg taaacccagc    39120
agatgctgtc tgtgctgtta acatcctacg cggtcatagg catgatactg accgtcagtg    39180
ggtatactac tggcgtggga cggtgtccag cgtgggtcga gaggacgact ttcagctgaa    39240
cttagaatgc actcacatgt tgactacact agcgtctggt ggtctgcgtt cacgttcag    39300 ctatacgtgc ccacacgcac tctatggtcc tagttgccga gctgccaagt ccgaggataa    39360
gaccaaggta tttaccgtca cctcaatatc gggcgctaag gtagggctgt ccggctggtc    39420
tgctactaac tggtggaacg gtggtcagct gaccttcaac agcgagaagt accgacgcta    39480
cataatgacc tcggacagta ctggcatact cctagatgcc gtacccgtag gactatccgt    39540
cggcatggaa gtgtcgttaa cggctggttg tgaccggacc aaggcaacct gccagtcgaa    39600
gttcaacaac ctagctaatt acggtggcta cttggctgtt cccgttaaaa accgtttca    39660
```

```
agatggtatt gcttaatatt agtaaaagga gtaattatgg ctgttcagct actctggtac   39720
gcagtaatac ttattgtatc agtgattgtg tctgtagccc tagcgcctaa gcctccgaag   39780
cctgactccc ctcagactaa ggacattaac gcgcctacgg cttcagagaa tgagtttatc   39840
ccggtagcct tcggcaccac atggctgcaa aagccaaacg tctgctggta cggtaatact   39900
ggcaccgatg aaattcgtaa gagcggaggt aagaagtaat gtccgatagg gtggaattac   39960
tccccggcga agaggacttt aggctataca tagcggactt cgatcaggag tccgttaagc   40020
agttcaattg ccatagcggg atgcgtgcca aaggcaaagc ctacggctta gattggtggg   40080
atttccttac taatggaatt atgttctcag agctggcagc tcttgaggat ggtcaaatta   40140
accgatgctt agtggagatt ttaaatgggc ggaggcggaa gtaagagcca agtcgtcggg   40200
tacaagtact ggggtgctat gcagctggta ctctgccacc gggggcttga gtcaattgat   40260
agaatacggg taggcgacaa ggtggtatct agtgaggtga tcactcagtc caactgccta   40320
aagtacatcg acaagtggaa cacgttcggc ggtgataagc gtgagggtgg tcctgtggga   40380
tttgcccgct tcttctttgg gcacgacgac cagcctgtta gctcgcttac tgagagtatg   40440
taccagagcg gtacagcttt ccgtggtgtt gttagtgtgt cgctgccaaa gatgtacttc   40500
tcagcaaaca acccatatat aaagccgtgg tcgttccgcg ttaagtcatt ccccgatact   40560
ccgggattag taagaacgca tgtaaagatt gacgcgggca acggtatagt gaacatgaac   40620
ccagcgcaca tcatatacgc ttgcttagta agtcgtagtg accgctgggg tcttgggctt   40680
aactaccaag aggacataga cgtaccctcg ttcgcgtccg cagcagccac gctgtatgct   40740
gagaagttcg gcatagggat agcgtgggag aacaactcag gagtagacga cttcatcaag   40800
gagatcctac gccacatcga cggtgctgtg tacgtggacc aagtctcagg gaagctgaag   40860
cttaggctat tccggggtga ctacactgtt agtaacctgc ccgttttaga cagctctgta   40920
gttaaagacc tagagaagtt cgactaccca cagtggggta acatcaccac acaggtcaca   40980
gtgagctacg tggatgccgt agaaggcaag gaaaagcctg taactgtaca caacatggct   41040
gctagggacg tgcagggtag agatgttcct gtggagattg acttccccgg aattaacacg   41100
cgttggttag ccacccgcgt agcgtcccgt gagcttaacc aactgtcacg tagattagta   41160
aacggtgttc tgatctgtaa ccgaaaagcc tcgaagcata acgtaggaga cgtagtaatc   41220
gtagacttac caaaccgcga gttagataag cgtatcatgc gtgttgtaga gaagagttat   41280
gggtcggaac ttaaggaaga gattcgcctc accgtgatcg aagataccct taaaactgtg   41340
gacccgttag taattgatac tggtgactcc ggttggacca gcctgatag cccgccgcag   41400 cctgtcgatt accagaagct ggttgaggct acgtactggg aggtgtctac gttcatcggt   41460
gacacgccta tcgactggaa cacgctgggt gacagctacg ggtttatccg tgatttggca   41520
gtcagtgatg taggattcgg atacgacatc tacgcaacca ccggaggggc tagtggcact   41580
tacacagatg ttgccgacgg tcagtttact aaccgagcgc agctggacgg cgctttgggt   41640
atgcctaccg gggcggactc tactgttaag atcaagggtg tgcaggacta tagcttagta   41700
atgctcaact cgcctgtcct aataggtggg gagctgtgct ggcttaagag tgtagacgta   41760
gcggcgagta cgattactgc gacacgcggt attgtagaca cggtgccaac aacacacagt   41820
gacggtactg aggtttggtt ctaccgagac acacgcacct cgttcgatga cactaagtac   41880
actatcggtc agacggtaca ccataagctg cttactaaga ctcctaacgg gattctccca   41940
gaaaaccaag cgtcggcaat aagctttacg atcaccggac gtgcccatag accttacccg   42000
```

```
ccagcacgac tacgcatcaa caacacgtac ctagggacgt cctctgggcg taacatgcgt    42060
atcgagtggg cacaccgaaa ccgcttaatg caatccgata aggtgcctat gccacaaacg    42120
tcgtcaagta tcgctgtaga gccggggact aagtacgagc tgaaagtggt ggggcttct     42180 agtggaaacg tagtccttga caagactggt atcgagggga ctctggagac gttggaccag    42240
aacgaccact tgtacaaact caaccgtgca gatagcagtg ttcggatcga gttgcagtcg    42300
agaagaccac atggcaacac caccctgacg tcgtttacta aatggaacca caccgtagct    42360
tgggctgctc ctgagactga tactgtcacg ccagctggcg gcgctccgta cacactagga    42420
gaccgagtaa atgacattat gatgcagtat cgcgactcgt ttgtagagta caagtttgac    42480
atatcagcgg atagagccgc gaataatgct cttgagatcg aggtccgcaa gctaaacatg    42540 caggggaga tgatccaagt agaagtattc cgtgacaata gccgtgtgca taacagcacg     42600
aagcaggttg gtagtatctg gcgtgtgagc tctcttgcag aaggagcata ccggatcaag    42660
ctgagtaaca ggtctactgt gacggatgtc aacatgctgg cgaggattgt accagcgtaa    42720
aactaatgct cacgtactag gcgcgtgagc cttttctgca actaattgag gtgatactat    42780
gaacgccgct gttaatagta agggtcggga tgacccgaac gtggttaaaa tgtgtccgaa    42840
agggcagggt acgaaggggg acggcgatgt gccaaacgac accagtaagc acatagctgc    42900
ggtactcgtc ctgatagttg ccggggcgat cacatgggct ggcttccagc ttagtaataa    42960
caacgcagca cttatggctc aggcggcagt ctcgcaaagc cagaatgacc ttttaaagca    43020
actaagttcc gatgtcagga tcatccaatc tggattagcg cagcaaaacg gggatctggg    43080
cgttctacga gcagacctca acaacacgat gagacgtgtt accggagtgg aggaccgaca    43140
gcagctcctc gacaagcagg tactacaagc tcttatcaat ggcaaacaag caaaggggta    43200
aaatcaatat gactaagatg cgcgagttta tcttgctcgc gctatccgtc gtgatagcgt    43260
tagccgtagt agtgggaatg gcagacccaa tggtattcgg tttactatta gtaaaaactg    43320
ccaaggcggt agtggcactg gtcgcggttc gagtcgcagt ccactacttg gataaggtaa    43380
tcggagtcaa cttccgagag catgtgcggg ggtgggatgg tcaagcaatg gctatttaca    43440
tgggtgctcg ctttattggt gctgccgttc tcttcggctg catctttagt tagcaacact    43500
cagtacgaca agtacatcta caaggcatgg gaagagtacg taccagagac acaatgctgg    43560
ttatggctga aggcgcaata ctaccaagag agtttgctgg acccggaagc tactagccat    43620
gtgggagcga tgggattagc tcagatcatg ccgggaacgt ggatagatgt tagtaagaaa    43680
cttaagttca atccgagagc atcaccgtac gacccgaagc tctctatcga agccggagcg    43740
ttctacttac gctaccagtg gtcacagtgg agagccaagc ggacctttga ggatagaatc    43800
agtttagcct ttgccggata caacgctggc ttaggcaaca tactaaaagc acagcgcctg    43860 tcaggggtc gggcagactg gaagtcgatt agttactttc taccggaggt cacgagagag    43920
aacagcaaag agactatcca atacgttgag cgtatctttc gctggaaaaa gcaactggac    43980
gaacaccgaa gttgtgcagt ttactaaaat gataatgggg agcttcggct ccccttgttt    44040
ttactaagag ggaattacta aaatgtttat tcgtttacta agcatgggcg gtacattact    44100
aaaaggacta tctgcgttat ggaaccgata caaattacta attgttatca ccctcgtcgc    44160
aggagctctc taccgcgcct attccatcgg gtatgaccta gggtctacct acgagcgtaa    44220
caaggctgtg gtagccgttc tggaagccac aaccaaggct cgcacggaag agttccagta    44280
ctataagaag caactgcgac ttatgaccga aaaacacaac aaagagctaa cactggagag    44340
agaaaatgct cggatacaag caaccatcga caacaagcaa cttactaaac aaccagcctg    44400
```

```
cgaaattagt aaagacgatg atgctaatcc tgttcttact aatgggtacg tcgagctgta    44460
caacgacgca gttcgagccg caaatcgagc cacccaagaa ggagataccg gaggaattac    44520
taaaacgatg cccaccgctg aaaacggtgg atagtaacga cccgtgggtt ttactaaaag    44580
tagccacaga gaatatagga acagcagcag tctgtatcct taactaccac accctccaag    44640
acactgtagc cgacagtggc gaaaagaca gcaactaaaa actattgaca gccatgctac     44700
agttcgtgta gtatggcttc cgaaccatat ccaactggag ataacataat gcttataaaa    44760
cctgagacgc tatcagttcg cctagacgta acccgcgtcc tttcaccccg ctgcgctatc    44820
ctgctggcga taatacagca cacgtacgac catagctgtg cgtcccacaa tgactgccag    44880
atgcacgaag gcaagcgttg ggtacgaatc agtaactctg agttccgaga gctaacaagc    44940
tttagtccaa ccacgattac taaaagtatc caatccctag tgtcgttcag tatgatcgag    45000
actaagactc ttactaaaga taaaggtgat gtggctaact ggttcacagt cagcaaggag    45060
gagtagtcat gcgagccttc cgacttcccg atattctgca atcggacacc acgagcttta    45120
acacagacct agcggtaaag attgggataa cgcccgctat catattggga agtgttgctt    45180
actcgataga agctctctac gagagtggga ccgctaagga gtatgatggg agctactggg    45240
ctagggtatc cacacgcaag ctagccgagc gattcccgtt cctgtctacc cgcacgatag    45300
aacgcgccaa gaagcatctg gtagatttgg gattagtaag aattgacttt attggatctg    45360
agatgatgga tgttaaagtt gataacacat cgtggtggtc cataaacgaa gattctatta    45420
gtaaactgtc cagtttaggg gataccgaca aaatggcgga tacccctca gaccgacaaa     45480 atgacgtagt agggtctccg ccagaatgtc gggggatca ccgtcaaagt ggcggacaat     45540
ataagagtaa tataaagag agtaaagaat cttctaccga agattctacc ctatctaagc     45600
gtacgcgtag gactcgtaag cagagaacta aggactttgg gattagtaag gggaacttac    45660
cacagcgtag aaagagaact gcgaagaaag agactgagct tactaaacac actttcgttc    45720
ttgagaagct gggaggtgaa aagtacgttc ttactaaagc tggctttgat aagctacttg    45780
attttattaa acgccaagac atccagctta gtgaagaaga gctcaacgca tggattgaac    45840
tcaacaagtc cagcttaggg ctgagaatca cctctaagac gcaggtagtc aagaccatcc    45900
agaattggct agctagattc aacgagagtg accgctggag gctcgataag cagttgggta    45960
agggtaacgc cccggctagt ggtcgaaacc gcccacagag gcttaacggg aatatcagcg    46020
acaagcacac ggaaagtgaa atacgcgtac caaaacactt acaaagatta gtaaataagg    46080
agtattagta aaatgaatga actaaacaag ttacgctcct tggcagaccg aattagtatt    46140
ggtcagttaa aggcgcgtcg aggggagttc ccagaaatcc tccgtaaact gccgaggct    46200 ggggacgatg tatctgcgta catgaagcca cgattccacc cgcgtgtgaa caagatgcga    46260
actcgcggca tcccacagct gcacagacgt agcacgttca gctcgttcga agccaagggc    46320
agtcttgctg gcaagcgtga tatggtccgc gcttacgcag agaacttcac ggagatgttc    46380
gaggagggaa ctgacctcgt gcttatcggt ggtaacggga ccgggaagac acacctagcc    46440
agtgcgctcg gtctgacact tggggtgcgt acctgcatga ttgctgaagc cagatccttg    46500
tacaaggaac tcagtgatga cgaccaacga tacttcgagc tgttcggtga tgtaatcccg    46560
ccgttcaagt tcgtgaacat cgagcgcgtc atgcaagggc ttatgagcgc attcgatgcc    46620
aaggtcaatc attgggacaa cggtgaggag ttccgcgcca aggaggagga gttccagaac    46680
ttggtagagc tgaacggttt actaatcttg gatgagtatg ccgctaccaa agtcaacccg    46740
```

-continued

| | |
|---|---|
| atgtgcttga acttccttaa ccgactggct acgtaccgat acgataatcg actaccgacg | 46800 |
| tgcgttatta ctaaccgaac ggaagaagag cttcgagagt acgactcaac ggcagcaagc | 46860 |
| aggttcttat ccagcgatgg tttagtaatt cgctttgacg agggagacta ccgtgcaaaa | 46920 |
| ggtcgataga cttcgacaag acttcaagcg tcttactaat caggagaaga atcaattcct | 46980 |
| gttctggctg gggctttctt cgcaggaagc ctcagaacgc ttttcagagc gtaagatata | 47040 |
| cgaatgcctt aagagctcac tctccaagct gtcagcagcc ggagatttgc aatttgaggc | 47100 |
| ggttaaatcg ggtcagactg gtgaacactt ccaaaaagta gttgagaagg tgaataccgc | 47160 |
| agctgaaacg ctccagccta atgagcgaga gcgtttctta gtaaaatact gcgctactgc | 47220 |
| tgttggtcgt ctggttgttc tggactcacc cttacaactt ccacatttac taagaatgat | 47280 |
| tgcccgtcat cacgagcaga tcatggggga cttaaaacgt gagctttctt actaagaata | 47340 |
| aacgagtact actcctcgtt gatgtatcga acataatgta taaggctatg cacatccata | 47400 |
| agaatcttac taaagatggt aagttcacgg gtggcattta cggttttatg gcgcaagtaa | 47460 |
| gcacggctat ccgtgagaac gaggctacgc atattgtgtt ctgttttgac cgcaagccgt | 47520 |
| acttccgtga agaagggctg agtattgact acaaagcagg tcgtgagaag tcgccagaga | 47580 |
| ctgaggaccg actagcccag actgaagacg ccgtacacga ccttactggt cacttcacta | 47640 |
| agtgggagtt cgatggtttg gaagccgacg acttgatcgc ctacgcagta aaacgctact | 47700 |
| accaccgatt cgacaagatc atagttcaga ccagcgacac cgacccttat caactgttcc | 47760 |
| gcgaagctga cactaagctg ggcttttgga agaaccagaa ggacggtcta tttacctacg | 47820 |
| ctgacttcat cgaaacatct gggttcacta tgggtgacga gtggttggca ttggacgcta | 47880 |
| tcactggcgg tcacaatggt atgggtaagg gcatcgtagg gtacggtcct aagaaagcca | 47940 |
| cggacctgat ccagaagcgt tcaagcaccg tacgcgactt gctctacatc tacccggatg | 48000 |
| cggggtacaa ctacacagtc atgcagctac cgcacgaagg aatccaccaa tacgacgggg | 48060 |
| aaatacgcct aggtcttaag agcatgtctc gtaaggacct tactaaattc tgcgcagcgt | 48120 |
| atggaattaa aatgcctccg gcatgggtag aaactttttac taaggttaaa taatggctaa | 48180 |
| gaacaagaac atgatgagta tcccggatgc tcaggacatc gtgacgctgg catgtttcga | 48240 |
| cgagaagtgt gctccgcaga tgttcgcctc ggtgacgctc aagcatttgc ctaacgacaa | 48300 |
| gctccgtgaa gtgttctcgc gtgcgaagga ctacttcgat gagtacggga tgcctatcgg | 48360 |
| ctctcaccta accaacgagt tcgctgacga gctgaatgac cgcaagcagc gtgcgcgtgc | 48420 |
| taatggctac cgagagctgt tagaaggttt gatggagaac tacgaggtag tcaacccaca | 48480 |
| gtacgttcta aaggggctga aggacttcct attcgtgcag gagatgcgtg gtaatattcc | 48540 |
| gaagctggtt gagcacttag aagacaacaa actggaagag gtagagaagg ttcttactaa | 48600 |
| actggcgtcc agtaagcagg aagaagactt caactacatc tgggcttcag acatggagca | 48660 |
| agtctaccac ggaatcttca accgtgaggt gggcgagagt cttgagatcg gcatcaagga | 48720 |
| actggatgag aacaacgtcc gacctaccaa gaaagagctg ttagtaatgc tggcacctcc | 48780 |
| taagcgtggt aaatcatggt tcggtgtgca gtgcttgcga gcaggcatac agaacaagaa | 48840 |
| gaagaaatgg aagactttac taattacgct ggaaatggca cacgttaagt tcggtgagcg | 48900 |
| ttttgtgcag aacctatggg gtcgctgttt gggcgagcct cagacagtgt cgagcaccat | 48960 |
| cattcatacc gacagtttg ggcacgtcca aaacattgac aatcagccgc gttatgagtg | 49020 |
| caagtctatt ctggacagagt tcgcagacga gaagcacgca gcgcgagaga ctgctcaatg | 49080 |
| gtttgagaag cactcgacag agcgtccatt cgtgttagcg cagttcccaa cgggttcttt | 49140 |

```
tactatgcgt aaactgagag cgttcgtgga ctggcttgat aaggtagagg gatggcatcc    49200
agaccagatt atcctagact atccgggtat catgaagctg acattaaca acaagcgcca    49260 agctatgaac caactctatc aggacttacg tggctttggt gttagtaata acatcgctat    49320
ggtagcattc caccaatcga accgtgacgg tgcgcgtgag cagacagtgg acgacgtgat    49380
cgatgagact aacgcaggtg aagacttctc ggtaacacag cacgctgatt acttgatcac    49440
gtacaaccag tcgccggaag agcgtgagct taacttggca cgtttgttcg taccactaaa    49500
ccgtaacggt aaggacaagt accagatcgt tattagtcaa aactatgcca cgggacaatt    49560
ctgcttaacc agtggatacc gtgacagtcg ttataaggat atggtagttg aggattcgga    49620
cgaagctgga gaaatccaa caagggagag gcgggggtg gagccgcctg cgggatacca    49680
aattgacgag tacgggaact ggttcgaccc agaaaccgga gagtcgtgga caggagcaag    49740
agtcgatgcc aacagttcgg gatttcttaa acagacgcct tgatgactgg cgctggttga    49800
aagacataga tgacgatacc gttatctaca atgaattagt aaacatgcct gtacgtccac    49860
agtttgagta cagaccttat atgtgtcaat tagtctgcca ctggatagga atctgccggg    49920
attccttcct cttcttcctg ccgttgtcgg caggtaagac caagttgata ctggacatat    49980
acaactaccg cctgcgtgaa gatgaggact tgcgcgggct tgttctcgtt ccgcgtgttg    50040
ctaacataaa gacgtggttg gatcaggtgg aggagcacac accgcatctg cacgctatcc    50100
ctattctggg tagcactgag gagaagcgtc gcgccctatt ctcagaagcg gacctgtaca    50160
ttgcctgtta cacagaccta cagttcttaa tggcagattt gcagcaagtg tcgggtaaga    50220
agaagcagaa gcgtaagcct aacgagagaa tgtgtcgtga ggttcagaag cgcataaact    50280
tcgtggcttg tgatgagatc cacaaagcgg gcaaccacga gtctctgatc tacagactcc    50340
ttaagcgtct tactaagact gctcgctacc gctacggcat aaccgctacg ccgttcagtc    50400
gtaaggtgga aaggctgtgg gcgatcttca acttgataga ccacggcgag accttcggat    50460
caaccctaac tcagttccgt gaggtgtttt ttactaagaa gagaaacgta tggtccgggt    50520
tcttcgagca caagttcgat gacagtatga agagcgagct acaccgcttg atgcagaacc    50580
gctcaatacg ctacgagaac cacgaggtta agaacttcc tccgaaggtt ccacgtgtag    50640
aagagttggc aatgagccct aaacagctgg agatgtaccg cgatgctcgt aagggtctag    50700
tcgattgtgg tagtggtgct aaggaagagt tagaagccgc gtacatacgc tcacgtcagg    50760
ctctttctgg ctacgtcgag tggaaggacg agaaccgtaa aacacaaggc atctacctcg    50820
atagcgacgc taagctggaa tggctgcaat ccttcttgga ggacacgaa gagaagtttg    50880 tgatcttcta caagtacacg agtagtgcta agcgcattac taagatgctc aagaaggaaa    50940
agtgcaagca ctcttggatc tggtccgggt gcaagaacgc agttaaatcc tacgatgact    51000
tccgcaaaaa ggacgacatc caaggcatgg tgatcaacct agcttctggg gacgctgggc    51060
tacagttcga aatggctcgg tactgcatct tctacgaatc accagaagac ccggtaacac    51120
gcgagcaggc ggaaggtcgt gtagcccgtg acggtccaac agccacagac agcacgtacg    51180
tcattgacct tgttactaag aagtcgtttg agggtaaatt actaaaatcg ctggaagaag    51240
gtatcaactt ccaagaggag gtactgtccg ggcgtataca ggactgggag gattagatgg    51300
taatgcttcg taagcgggtt gttcacgagc gtacgaaggg tggcaggctc cgggctaaga    51360
tagttcgtga gcctgttacg catagtaaac cgcaaccgcg aaaacgcaag aaacgaaacc    51420
taaaggactc agaacacagc cagctctgct tgttagccaa gaagtggatt cttaagaacg    51480
```

-continued

| | | |
|---|---|---|
| ggtttggggt agctattgat gaccggatga aagcagcctg cgagactggg gagcagcccg | 51540 |
| acgctatggg gtggaatgct tccgttagta tagtgatcga ggttaaaaca tcccggtctg | 51600 |
| atttcctcgc agacaagaac aagaagttca gagcaaaccc aaggcttggt atgggagact | 51660 |
| ggagattcta tctgtgccca aaaggtctaa ttagtaaaga tgaggtcccc gaaggatggg | 51720 |
| ggctcctgta ctaccacgaa ggcaagatcc gccgggtgca tggcggtcct aaatccaacg | 51780 |
| ggtggtcgtt cgacggtatc ccctttgtag gcaacaaaga ctgcgagatg tcgtacatgt | 51840 |
| atagcgcact tagacgtatg gttgtgcgtg gacacttaga gtcgatgtac tcaatggatg | 51900 |
| gtattaagaa atgagtattt tcaaacgcag aggaacagat gcttggattg agatctttca | 51960 |
| caagcacagt atcacttacg cgacaaagca taagaactgt aagcgcggta acatagtaat | 52020 |
| agactgccct ttctgtgcaa actcagaagg caagttccac atgggtgtgg acaaacatgg | 52080 |
| tcgcttcggt tgctggaaga accaagagca ccgggggcac tcaccgcaca agctacttgt | 52140 |
| cgccttacta aaaatatctc cagccgaagc tacacgccta gtcggtgcag acgaaggtca | 52200 |
| ggtggacgag gacgagtgga actcgctgct acgaggtctt aagtcgtggg aggaagaaga | 52260 |
| aggcgtatgg gacgacgagg aagaggaaga agagccagct aaggtgatcg gtatgaagat | 52320 |
| gccaaagcag ttcatcccaa taccccgaaa cggtccggcg acagactact tctactactt | 52380 |
| gatggaccgt gggttcccac gcaaggacgt tcgcaaatta gtaaaacact tcaacctacg | 52440 |
| ctgctgtgat gtgtgggatc gtgttgctga caagatatgg tacgagcgca tcatcacacc | 52500 |
| cgtgtaccta gaaggtgagc ttatgtgttg gggtagtcgt actattaacc ctgacgacga | 52560 |
| gctgcgttat atgtcgctgc cagcggacga gagtgtgatc ccggttaaag agctggtata | 52620 |
| caactatgac aactgtatgg agggtggtaa gatactgctc ctagtagaag gtcaggtgga | 52680 |
| cgtatggaaa ctagacttct atggcaagca gcacggata cgcgcagctg gtctttttag | 52740 |
| taagtctatt gttcctagtc aggtagattt agtaaatgag ctgaagaagc agtacgacca | 52800 |
| cacattccta ctgctcgatg cccacgagga agcttacggg ctatcattat gtgatttact | 52860 |
| aaacgggtac ggtaagcgcg ttaagaccat catgtgggat ggtaacgacg aagaccccgg | 52920 |
| agcggctact ttaaaagagc tagaaacttt ttttaaaaaa ttactaaaaa agactttact | 52980 |
| aaaacgaacg agggaagtac tattacctcg tcctcaacga agaggggcaa gaaatgaatg | 53040 |
| aataccacgc gaaattagta aaatctgatt tccaaggcgt tcgagagatt tgcaaggttc | 53100 |
| cgcatccggg aattgcaggg cagttcttta cgtactttga ttttgacgat gagaacttgt | 53160 |
| tgggcgttcg cggaccgcag ggaccacaaa tcttcaaccc atctacttct cacactcaca | 53220 |
| tgggtgacgt gctgattaaa tggatggaaa caggtgacga agaagttttt actaaactta | 53280 |
| aacagttaga gcaaaaacct cgacgtcgaa aacgtttaaa agttgtcgaa gaagagtcaa | 53340 |
| aaacaactcg gaagcgacgt atagttaaga caggtgatga tgatgtcaat ccaaaccaac | 53400 |
| gtagaccacg cccaagaccg ccacacgaaa ccttccgagc agacttggaa gccagtattc | 53460 |
| cacggcgaaa tcgaagggta cgtaatgaac tgggttcgca caaccactg gaaagtaaac | 53520 |
| cagcagcttc cagacgtcga agacgttaag caagaagcgt actgcatttt cctttacgtt | 53580 |
| gcggataaat acccgaacat tgataatcca cgttggttta tggatatgtt caagagaact | 53640 |
| ttcggttgtc gtatgattga ttgttctcgt aagcagattc gccacaaaga acacttcgcg | 53700 |
| gaaacggacg tattgtttag cgaaggagaa gaaagcctat ctcttactga aatgatggta | 53760 |
| ggcgatcttg aaacctcggc tattgctgaa aagctaatgg aagaggctga cggggaagtt | 53820 |
| aagcaagtgc ttcgtacact tctaaacatg ccagctgaag tctttactat ggttgaagaa | 53880 |

```
gcatggacaa gtcgcggaaa gcgtaaggtt atgggcaatc aaatgctttg cgccttactt    53940
ggtaaagacc caaccaagac cgatctagtg aaaaaagttg aagaacactt tatcggttaa    54000
ctaaaattgt tcgtatagac actgtacata cgaaattaac tcagttaaca ttactaaaga    54060
aggtaaagac tatgtcattg actaaagaaa tcctacaaga acttatcgaa gcgactaaca    54120
ctccacgtgc taagcgtgac tcgcacgaga agcacttgca gaaaatcatc aaggcagttg    54180
gcgctctgga cgacgaccaa tgggacgctc tttcggacga agctgctgaa tggtacaatg    54240
acgcggttaa cgcaataaac gatggtcaag acattccggg tgctgataaa gacccaatgg    54300
aagagaccga agaaaaacca gcgcgttcac gccgtggacg taacacagaa actgacgaaa    54360
cggaaaacaa accaatgaaa aaagttctag tagcaatcgc acttgcagaa gtagttaaag    54420
gcatcacagt aacagtagtt tgcggtgacg atacttttga aggcgaagta atcgacgtta    54480
ctaaaaaagg tcgcggcaaa gcagctaaag ttgaagagtt cactctgaag actgcggacg    54540
gcgaagaagt gttcggcgct gaagacctaa tcttcgacga aggtgacaag atcgaacgtc    54600
acgacgaagt agctgaagaa gagaaaaagc ctgctcgttc tcgtcgcggt gctaagaaag    54660
acgagccaga agctgaagaa aaaccagctg gtcgcggttc tcgtcgcggt gctaagaaag    54720
aagagccgaa agcggagcca gtagaagttg aaaccgagat cgcgttcaac gacatcgcta    54780
aagacgacaa gctgaagctt caagtcgaag acgacgcttt cgaaggcact gttaaagcgg    54840
ttaagaaaac tggtcgcggc aagaacgcta agtagctga gttcacttta gtaacagcag    54900
acggcgaaga agttttcgaa gcggaccaca ttgtggttga agaaggcgac aagatcatcc    54960
gtatcactat ggaagagcaa gcgccagcta agaagaaaa agcagcaggt ggtcgtcgtg    55020
gtcgcggtgc taaatctggt agcgcacctt cagcagctca ccaagttcgc cagcttatct    55080
gtgagaacct agactcagac aagaaagcga ttgaagagct aatggctgaa aaaggcatcg    55140
acatgaaacc gtcaacgttc gatgtacttt acagcgaagc gcacagccta gtagcagtaa    55200
tgcgtgaact agacatgcta gcgtaattcg gtacagtgta gccggataga gattgggag    55260 cttcggctcc ccttttttcgt attagtaaga cgaggtttag taaaatggaa caagagaaat    55320
tcatagacct tccagagctg cgtatgctgg caaagtcgaa agcacaacac acgctacaca    55380
gaggtttaac tttagtaaac cataaagggc atacagccca cgtattcggg ttcactacgc    55440
tggacctact agcagcttca atcttcgcac aagaagccaa cctgctctta gcatcccagc    55500
catacaggac taccaacgac catatcctgt tctttacacc aacaagccgc ctagagctcg    55560
cggacataat cgttgggttc aagtacgacg acaacaataa ccccagcaac gtccgacagc    55620
agtattcggt cctcaatatg gatgtttgcc cgacaatggt ccagctgaca cctccgggaa    55680
cagactggaa gccttgctgg aatagggct tgcactacgg accaagactt agtatagtta    55740
cttccggcaa tgttaatctc atccgttgga tcttgtaacg tcttggcttg ttacactagg    55800
gaggctatta tagtctccct ttcttttgtc tgccgtatag gttcggacaa ccaaccaagg    55860
agaataacat ggctacacta gagaaagccc aactacagcg cgtattgaac ttcatcaagc    55920
ctgcgctatc ccctcatgat ttcgttccgg tactatcaca cttctgtttt acggaagaag    55980
gtgacgtgta cgcttacaac gacctagtag gcgttactgt acgtgagcac gacttcggga    56040
tcgtgggtgc tcttcccggt aaggatttac taaagtaat aggctccttc ggcaaggctg    56100
aagttagtat cgcagagatt gacgacggtg ctggggtgct tattaaatct gggcgttcaa    56160
agactaaatt agtaatgcta ccggacgatg acttcgttta cgagcccgtt actaacacag    56220
```

-continued

```
accagaaacc tcgtgtagag tttgaactgg acgaagagtt cttaactgca ttcaagaagt   56280
gtatctctgg tatcggtgat gaccctacca gccctgcaca gatgggtatc acgatcacgg   56340
acagtttcct gttctctaca gacaacgtca caatcaccgc gtacgagctt ccagacccaa   56400 ttgagggga tggtcaagtg atactgccaa aaccgttctg tgagcttgtg gtagagcttt    56460
ctaagtacaa taagtcggag attatcacca tgtcgttcta cgacgacaac gtgacggcta   56520
ttctggagga tgagtcggta gaaattacta cacgaatcct agaagatgac gagccattcg   56580
actttgaggc agtactcgac ccgttcctag aagatacga cgccttagta aaaataccga    56640
acgagtttaa agacatgttc gcacgcgctg aagcggtcct aggaaaaggc gacgaagcca   56700
tactagacat cgcagtagaa ggggacgttc tgtttatctc ggctaagtcc ggtaagatgg   56760
agctcgacga tgaatgcgac tttgactccg acgacgttaa gttctacgca gatgcaggca   56820
tgattgcccg tgcttgccaa tttacaacac acgcagccct gctcccagca gcaatgttct   56880
tcagcgacgg aggggcgttc taccacctaa tcagccactg tgaggaataa cgatgggatt   56940
ctttcatact aagggagcca aaggcggctc ccgacgttta actggtaagc agcaggcatt   57000
cgagcagcag aagcatttac taaaatcagt gggtgctaag aagttcgaag gcgtaggcgt   57060
gcagcctgcc gggtctgata atccgttttgt gtacatccta gggcttaccc caacgcctaa   57120
ccaactgcgc agaaacgacc ttactaaagg tgagaccgca caggttatgc gtaagtactt   57180
tggtcgtgac ttctactaca acgactgccg tcacggagct gtagtacgcg agacgtttgc   57240
tgagctggac gaagtgatcg acgacgtggt gatagagcag tggcgtggta ttaccgagca   57300
ggacatcgaa gagactaagc cagcggtagt tgtcgtctg ggtgctggag ctttacgctt    57360
cttcactggc agtgctgaca tccacggtat gcacggcaga atgctacccc acaaagtggg   57420
taatcacacg ttctggctac tcccggtgtt tgacccacgt tgggttatta gtaaagacca   57480
cgacttcttc gtgaacgagt acgagatctg cgttaagacg caggtcagtc gcttgatgga   57540
cctgatcgaa accgggagcc taccggagcc tgttgtttac gacagtaact acgacgatgg   57600
tatcgagatc atcatgggtg agggcgtggc agatgtacat cgcgtagaag atgtactgca   57660
tgacatgctc aaagagccgt tggtatcggt ggactacgag acgcaaaacc tgcgcccgta   57720
cctagaagac tcacgcttac taactaccgc cgtgggaacg tttgaccgta ccgtggcgtt   57780
cccggtagac caccctaggg cttggaacaa taagactcgc cgtcaggtgg tcggtctgtg   57840
gggtgagtac ttgtgtcagg ctcctcgcgc tatcgtttac aacgctacga tggagcaaga   57900
gtggacagct cactactacg gttttagtaa tctgcgtaaa acccagtggg aagacctaat   57960
ggcagcagcc tactgtctgg actcacgtaa ggggcattta tcgttagatg acttcatcaa   58020
gtacaactgt ggcttcgacc tcaagaagct gtcaggcaag atgaataaag ctaacatggt   58080
gaatgagaaa cttgaccgcg ttcttatgta caacggacga gacgttaagt ggaccttcaa   58140
gggattcgag atcgcccagc agcgtttaga gctggaggga gaagaacgtc cttaccatac   58200
taaggttcgt aactctgccg ctctgaccgg gatgcaaatg cgcggtatgc cacgtaacga   58260
ggagggattg attgaactgc gagacatcct tactaaagac atcgcggata ccgagcagga   58320
gctgatcaag acgccggagg ttcgtaagtt cgagcgcatg aacgatatgg actttaaccc   58380
gtcgtcacca gagcataacg tcacgctatt ccgcgacatc ctcaagcgca aggagggtaa   58440
gaaggaaggt aaggacaaga agggcaacca gaagtacagt accgacgaag cggcgcttag   58500
tgccatgccc gccgctgagt gtccttcagc gcctcttatt ctgaaactac gtggttttac   58560
taaacttaaa tcgacgtatg ttgacggtct tctaactccg atcacagagt tcatcgggga   58620
```

```
cgagaagaag cgtaagggtt tggtgtaccc ggatggacta ctgcacccga attacaacgg    58680
gatgttcaca gccacggggc gcttatcttc ggacgagccg aacgcgcaga acttccctaa    58740
gcgtaagaac cgccacatcc gtaagccaat agcaccacct ccgggattcc gggtagtctc    58800
actcgacttt ggtcagattg aggcgcgtgt attcggtatg gcgtcacgag accctaactt    58860
ctgtaacgca ctgtggaaca acctagatgt tcactttgac tgggctgtta aaattagtaa    58920
cgagtatccg gggattctgg atcgaatcta cgacgagtac tacgacaaga tcatcaagat    58980
ggtcgatggt ggtaaatcag agtacgactc gatcattaag tgtcttcgtg gtgacgttaa    59040
gaaccagtgg gtgttcccgc agttcttcgg agcaggcttc aagtcttgtg ctcagagcct    59100
acacatcccg gacgagaacg cagaaaacct acgcgctatg ttctgggaag agtttgctgg    59160
ggtgcaggag tggcagaatg aaacgctgga gcgtgcttac cgagacgggt acgtgagaac    59220
tctaaacggg tttaagcgtt ccttccctat gagtaagcag gagatcatca acacaccgat    59280
acaaggcacc gcagccgaag tagtactgga gggtctgtgc ttactaagtg aggaatccgc    59340
tctactggaa gacgtgtaca tgcaccctat catgcagata cacgatgacc tgacgttcat    59400
catgccggag gatggtatgg acgagcgtat aatgcacgta gcggagatca tgacgggcgt    59460
gtacaagacg tttgactttg taaacgtccc attgcttatc gaagccgagg aaggacctaa    59520
ctggtgtgac caaaaggttt acggtgagta ctcatctacc cagttcgggc atatccgcgc    59580
tgactaatca aagcctccct agggaggcta ttttactaat agtaacgagg taacaatgaa    59640
acagtatcta gcacttgctg agcgtatcgt ctctgagggc gagtggatcg agaatgagcg    59700
cacgggcaaa aagtgcctta ccgtgatcaa cgcggactta gagtacgatg tgggagcaaa    59760
ccagttccca ttagtaacaa ctagaaagag cttctggaaa gctgcggtag ctgaactgct    59820
gggatacatc cgtggctaca gcagtgctgc tgacttccgc aaactgggga ccaagacttg    59880
ggatgctaat gccaatctaa acgaggcgtg gctaagtaac ccacaccgcg aaggctacga    59940
cgatatgggt cgtgtgtatg gtgtgcaggg tcgtgcttgg acaggctcgg acggcactgt    60000
ggtagaccaa ctccgcaaga tcgtggacga tattactaag ggtgtggatg accgtgggga    60060
gatccttaac ttctacaatc cgggagagtt ccacctagga tgcctacgac cttgcatgta    60120
tagccaccac ttctcgctac tgggagacac gctttactta aacagcactc agcggagctg    60180
tgacgtaccc ttgggtctta actttaatat ggtgcaggtc tacgtgttcc tagcaattat    60240
ggctcagatt accgggaaga aggcaggtaa ggcttaccac aagattgtta acgctcatgt    60300
ctatgaagac caactagaac tcatgcgcga cgtacagtta aagcgtgaac cactaccgct    60360
acctacgctt tggattaacc cagacataaa gacgctggaa gacctagaga cttgggtaac    60420
agtggacgac ttccgtgtgg acgactaccg tcaccacgac ccaatcaaat atccattctc    60480
agtttagtaa ggagaacagc aatggaaaca agaccactac acgtatcact acgcccacag    60540
acctttggcg agatcatcgg tcacgacgct gtagtaaaag acgtgcagaa tcagctcgat    60600
aacaacaacc aacgctgcta cctattcatg ggtcccgcag gctgtggtaa gactacttt     60660 ggtaatgtca tcgcacgtca cgtagagtct aagaacatca tcgaagtaga cgcgggtagt    60720
accagcaaag cagagcagat ccgtgagctg gtagataagg ctaagtaccg tgggtttggt    60780
gaaaacccta tccgcgtcta catcttgaac gaagtgcagg ctcttagtaa ggctgcttgg    60840
gatgccatgt tggacatcat ggagaaccca cctcaacacg tgtacttcat cctgaccact    60900
acggaatccc cgaaggtgcc taaagctgta aagactcgct gcgcatcgta cgagcttaag    60960
```

| | |
|---|---|
| ccgcttagta agaaggctat taacgacctc atcgacatgg taatggatga agccgatatg | 61020 |
| gacatcccgg acgagttcct agacgtggtt gccgacaagt gcgagggctc tccacgacag | 61080 |
| tgtatccaga tgctgcttaa ggcagagtcc gctaagaacc gatctgagct gaataccctc | 61140 |
| ctagatgaag ccgagagcga taaccagatt atcgaccttg ctcgaacact cgcttttact | 61200 |
| aaaggtaaaa aatgggtaa agtgcagacg atcttgaagg acctcaagga cacaccacca | 61260 |
| gagagcatcc gtattgtagt aactacgtac attgctgggt gtatgctcaa tgcgaagaca | 61320 |
| gaagcagacg cagagcgact acaccacatc ttggatgcct tctctacacc atgtaaccct | 61380 |
| accgacaagc tagcaccgat cttactagca tgtggtgaca tctgcttcgg ggagtagtaa | 61440 |
| atggcatacg atgtaggtga gcaagctatc cgctcgttta agaaccgtct acgtatagat | 61500 |
| aagaacgatt tggacaacga gctggtagag caatcacacc tcttcttcga agtatctgag | 61560 |
| cgccttactt gggctaaagc agaacgtgat gaagttaagc gcgagtgtga tgagctagcc | 61620 |
| ggggaactta agcggacct attcgcagaa aaccctaagc tcgctgacac taaagctaca | 61680 |
| gctatcgtga aaaagatcc tgactatcag gaacgttacc gcgaaaaatc tgacgcggac | 61740 |
| cgtatagttg gagcatggga ggcattagtc gaagcgttta atcacgcgg ctacatgctt | 61800 |
| agacaattag cagacctcta tgtggctaac tactactctc caattagtgg tggtgagtct | 61860 |
| caggacgata agcgtcgcaa gcgtgcggaa cgtgatgacc gcagcaaccg acgtagaacg | 61920 |
| cggagaactt aacatggtg ataatttgca gctggcagca gcaattatgg tattattccc | 61980 |
| gattggagcg tatgtattag ctcgcatggc aacaaaggct tactttttta gcaagctaga | 62040 |
| atttcttact aaagtaaac agaaaggatg gtaaacatgt cacgacgtaa tcgtaacagc | 62100 |
| ggcggtcgta aaggcttcga gtacaagaag cgttctaaag aacaggtgca gaagcgtgcc | 62160 |
| gaacagcagt caggcgactt taagtcaatc ttcaaagaag gcatcaagat gtacaagcct | 62220 |
| aagaagggtg acaacgcaat ccgcatcctt ccggctactt gggaagaccc ggatcactac | 62280 |
| gcactagatg tacacatcca ctacggtgtt ggtgctgacg aagagcgcgt gctggcactc | 62340 |
| cacgagatgc taggtgaaga cgacccaatc cgtgagatgc gtatggagta cgaagccgac | 62400 |
| ggcaataaag aaatggctaa ggcttgtcgt ccgggtcgcg cttgtgcaat gtggatcgtc | 62460 |
| gatatggaca acgaggcgga aggtcctcag atgtatctag caccaccaac ggttgacgct | 62520 |
| ggtatcgctc aggttagtat cgacaaacgc tctggtgaga tgttcgacat tgacgaccct | 62580 |
| gagaacggat acgaagtcta ctttactaaa cagggcgaag gtatgaatac caagtacgta | 62640 |
| ggcttccagc ttgcacgtac tccgtctgaa gtagatgaag aacacttgga ttacgcaatc | 62700 |
| gacaacccga tcccggactg cctagtttac ctagagtacg aagagattga aagatgatt | 62760 |
| gcaggttgga ctccaacacc tcgtggcaag ggtggtaaag atgacaaggg caaagaaaag | 62820 |
| cagaagtcat accgtgggcg agatcgtgac cgcaatgatg gtgacgacga tgatcgtgat | 62880 |
| tctaagtctg gtggtgatcg cggtgatagc gattacaact acgatgatgt acttaaagcg | 62940 |
| gattgggacg agcttgaaga catcattgag ctggaagagc tggacatcga ccctaacgac | 63000 |
| ttcgacgaag acgacacgga aggctgtgct aaagcaatcc ttgaagaact gggcattgag | 63060 |
| aaacctaagc ctgctcgctc ttctcgcggc gggcgtggta gtcgccgtgg tggtgatagt | 63120 |
| gatgatggtg attctcgatc ttcccgccgt cgtggtcgtg gcggtgacga tgatgaccgt | 63180 |
| agcgaacgtg ttcgcggtat gcgtcgaaat cgttaagaag tatccaagtg atatagttta | 63240 |
| gtaaaccaag ggggcatatt catgtcccct ttattcagtt aaggagatta gtaaaatgag | 63300 |
| ccgaggtatt attgtagctg tagaaggctt tgacggttct ggcaaatcca ctttagtaaa | 63360 |

```
gctgctggta gaaagagttag ccaactacga agtgaaggtg gttcaaacac gtcagcccgg   63420
aggcacgcct tacgcagaga agatccgcga cctgctaatg tctggggacc gtgaccgcag   63480
tcaagccgta gaagcacact tgttcttagc cgcccgccaa gacctatgcg ataggctggt   63540
agcgcctgcg gtagaagagg gggctatcgt ggtgtgtgac cgacattacc tatcgtcact   63600
tgcaaatcaa ccacagtgcc gatctctgtt cttagaaaac cgagtgtttg acccggacgt   63660
ttggatcatg gcgcgatgtc cgttcccggt ttgcatccaa cgcagtgagc agcgtggtga   63720
cgacgatgcg tttagtaatg acgagctccg cgagaagcgt gcccagtatg accgctacca   63780
gcatggtatc aaagacattc taccgttcac ggcgggggac tcactgttca cggtggacac   63840
cgacttaggt cttacaagtg cgcgtgagca gatcaagaaa gtagccagct acttagtaag   63900
cttaaataaa caactcccgt atagttcata gtgttccact cactttaagg ttagtaaaat   63960
ggcagagaca agacgtagac gtactaaggc agatgagaaa gaagaggctc ctaagtcacg   64020
ttcacgccgt acacgttcca cggaggctga gaagcctaaa gaacgtgcta acgcctactt   64080
tgtatcgaca gagaagggag tagaaggctt cagtaccggg tgttgtctgt ttgaccaagc   64140
cctaggtggt attgggtggg ctaccaagcg tatcatcaac atagtaggcg ataagtccac   64200
aggtaagacc ctcctcgcta tcgagggggat gatcaacttc catcgcacgt tcatcgacca   64260
aaacccacgc attatttaca aagagtgtga gtctgcgttc gatgagccgt acgcagaagc   64320
tctgggctta ccactcgacg acattgaggt agacgacgac cttgataccg tagaagacat   64380
gtacgaagac attgagcgta tcgtacaaga agcagagcgg gacccacgcc ctatcttgta   64440
catcgtggac agcttagatg gtcttagtga tagagccgag cagggtcgta agattgacga   64500
agccagctac gggcaggata aagccaagaa gttatcagag ttcttccgca agaagaaaaa   64560
ggtaatggct aaggctaaca ttactttact aattatcagc cagatccgtg ataatatcaa   64620
cgcggctgcg ttcggtaaga agtctaaacg ctctggtggt aaggctttgg acttttactg   64680
tagtcaagtt gtgtggctag ccaacttagg taaagttact aaaagctgtta agggcaagaa   64740 gcgtatcgtt ggtgttgaca tccgtgcagc cattgagaag aacaaggtgg gcaacccgtt   64800
ccgcacagct gactacccga taatttttgg ttatggggtg gatgacatct acgcctctgt   64860
agagtggcta cagtcgaacg taggatggga tgttcttgag gacctaggat tcaagaagac   64920
aacctacaag gctatgtgcg ctaagatccg tgacaagggt ggtcccgaag ccaaggagat   64980
gcgcgaagct cttaataagt tagtaatcca ccactggcag gacatcgagc tagacttgat   65040
gcctaagact ggtaagtatt agtaaaggag gcagtatgcc tgtaatccaa gcagccgaaa   65100
aacccactac gctatcctgc attcgttggg agggtgataa cctacgtgaa gtacttgagt   65160
tcaccgggaa gcactttaag tttgacaagt ggttcgccag cttcgaggag tacgaagccc   65220
atgtacgatc tgagggtaac atcttcaagg tattcacccg aaacggtgtt actgaagcag   65280
ccgtaggtga ttcacattatc cgtggggtag agggttagca ctatccatgc aaaccagaca   65340
tctttgacga gatctacgat accagtgggc gtgtgtttgt acctatggca gacgctagca   65400
cgcaggagtt agcggcgcgt ctggaaaaat gcaaggggta cgaaccctac atgcttaact   65460
ggatctgcgt gtcgtacaaa gagtgtggta tttcccgcat cccagtctac gagtgctacc   65520
acccggacca caccgtgttc tacgcaagct cagagttgca gcaggcagta gacgcattta   65580
gtaactaccc ctacctaggg tagcgtatcg taactagggg gcttcggtcc ccttcttcaa   65640
ttggagacca atatgatcaa cgaagacctg tacatggggc tagactgctc cctcaacaac   65700
```

-continued

```
tcaggcatag tggtctttgg taaaactact ggatacccttt atgaaagcat taagccgaag    65760
tgtaagggat atgagcgcct tgcttatatc cacgatagtc ttactaaaat actcgctaaa    65820
tacccaaaca tcaaaggcgc taacatcgag cggtatgcct acaacaaagg tggtaatgac    65880
aagtccaacg ccgggatggt atttaacatc ggtgaaggcg gtggagtcgt gcgactggcg    65940
ttattttcgg ctggcatacc tgtcctgctc actagcccaa acactgggaa gaagtacgca    66000
actggaaagg gtgttggggg caaggagata attctcaagg aagtgtacaa acgcttcggt    66060
gaagacctcg acgacgacaa cttagccgat gctttggtaa tggctcgtat agcttaccac    66120
tggttcacag acgactacga aggacttact aaggctcaga tagaagcggt taaagcagcc    66180
tctcttgagc atgagccccc taagcctact agccgtcgta aacggagagt aaaacgcaaa    66240
tgaatcgttt gattgctgcg gatacccact tcacacccaa gccgctagac gagtaccgtt    66300
gggggctttt tggctatctg aaggactggg ctatcaagta cgacgttgcc gagatctgga    66360
tactgggaga ccttaccgat gctaaggaag gtcactccgc tgagttcgtc aatagattag    66420
taaaccacat caccgagcta tcggaggtag ccccggtgtt tattttaaga ggaaatcacg    66480
actatgctag ggaacatgtc gccttctttg agttttttacg taagctgcct aatgtgtatt    66540
ggattgaccg ccctactact gtctatggcg tccgtgcttt cccacatagc aagaaccctg    66600
cggaagattg ggcaacacta ctcgacgatc tggacgagta tgagtacgcg ttttttccacc    66660
aatgtttcgt gggttcgcgc tcaagtatgg ggcatatcct cgacgaacg gacttagacc    66720
ttactaaact taaaaagtgt aaggtgtacg ccggggacat tcacctacct caaaccgtcc    66780
gtgggattga gtatgtggga agtccctacc cgacgacgta cggggaccgc ttcctaggac    66840
gctgcttact agagacaccg gaagggcgta cccagttgca ctaccctacg atccagaaat    66900
gcacgctagt ggtagagtca gtctcggaaa tttatgacgc ccatgtgtat ccgggagacc    66960
aagtcaagat ccgctacaag attagtaaaa aggaccgggc ggagtggaca aacatcaaaa    67020
acgccataaa agctgcctgc gatgacttgg gagtggtgct aggtggaacg gagcttgtca    67080
cagacgtggt agaaaaggct gagttgaagg attccaccac taaggtgact aaaacctctg    67140
agaaagccat tctgacgcaa ttcgcccata aggaagattt accagatgac taccttgacg    67200
tagcccttac tattctgaag gaggagtgat ggactttata ggcattcgtg gggagaagtt    67260
taagagcttc gtggagccct ttgacttcac cctaaacaaa ccaccgggac tgtacttact    67320
aaaaggcgag aacgtagccg agccaagcct aggtggtaat ggtgtgggca agtccaccat    67380
ttgggatgcg ctgttctggt gcttgaccgg gactactttg cgtaagctga agaacactga    67440
cgttaaaccg tggggaactt ccggcagtac gtgggtggag gtcatgatcg cactggatga    67500
ggatttacta acagtgcgcc gacaaactaa ccccaacgcc ctaacgttag agtctgatat    67560
gcaccagaca ggaccgcagg acatctctac agaggaacta ctccagttct ttaacgtgga    67620
cgagacccag ctactccact ctcttatcgt cgggcagttt ggtacattct tcttcgacat    67680
gcttccagcc aagaagcagg agttattctc ctcgatacta tcgctggacg tgtggcttac    67740
acgtagtaag acagccgcac agatggtgaa ggttcttaag attggtctac aagaggcgga    67800
gcttgagtac gggcggctag agtcgtcgct tgagatgctt cgggctgtag cctatgacgg    67860
agactctgaa gactgggaga acgccacgc cgaggactta gcagagtgtc aggatagaat    67920
atcggatatt actaaagagc tagaaggtat cgacgtgtca gccctagagt ctgatcgggg    67980
ctggacggag cagctgctga acgatactga ggctacgatg cgtgaactgg tcaaagagat    68040
cgacgctatc aaagaagaca ttcgggaagt tgagaacgat aagcgcgatg cagacaacgc    68100
```

-continued

```
tatcgacgac ttgctagagg acttcgagga tactcttagt aaaggcacgt gtaattactg    68160
tggtcatgag gtatctgaca gggagctgga ccgcttagag gcttcgacta aggttaaggt    68220
ggatggttta gaggacaaga tagacgagta taacgacgag cttgctgacc ttaaatccga    68280
cctagcgcct aagaaggagt acctagagga caggaagagt gaagccgctg gtttgagcga    68340
taagcttagt aagctggatt ctgacattcg aatggctctc aaggaccgta agagtttatc    68400
ccgcgacctt agccgtgcag aagacgtcta caagaagtta gagcgagaga ctaacccttg    68460
ggctaagctg cgtgactcga acgagtccga tgctattgag atgggtgcga agctggtaga    68520
cgctaacgag acgattagta atctgaacac ggctattgag cgtaccaact actggatcaa    68580 gggcttttaaa gacgtacggc tctttatgat cgacaactac ctagtagacc tagaggtgga    68640
ggttaacaac tccattaagc agctaggttt agacggctgg cgtatagagt tctctgtaga    68700
ccgtgaaacg cagcgtggta cggtcaagaa gggcttcgag gtttacgtgt actctcctcg    68760
aaatactaag cctgttaagt gggagtgttg gtccggtggg gagtcctccc gtcttaagct    68820
ggcaggtgag ctgggcctta tggagatgat cttcacggct accgggcagg agcctaatat    68880
cgaggtgttt gacgagccca ctagctttat gtcccaagag ggtatcgagg acctgctgga    68940
actactaagg gaccgtgcct tactaaaaca aaagtgcatt tacatcatcg accaccactc    69000
agtcagcttc ggcggctttg agggagtcat taccattcaa cgcgacaact taggaagtcg    69060
catactggag aagtaacatg attcatttta ctgttagtaa aaacgcaaca atagcccacg    69120
cttgggttcg caacgtcctg tccgcagagg gacagattcc attcagcact atgatgcttg    69180
atgtggagtt cagcttccat gccgagtcgc tatcagactc cgacgacgta gccccgcacg    69240
agtacctatc tgtgtacgct gggcaagtgc tggaactgtt tgacggcgta cacatcctgt    69300
gggacaagga cgagcgtgct caagtggtaa cagctgaaat tcacgagtac tacggcgggg    69360
tgcggtcact aagtacaccc tacaacccaa cacttgagca cgtgtccggt atgatctacg    69420
cggtaatgca ccgcatcctc tgcgcgagta actttactaa ctcagaagac ccggagctgg    69480
agcttgtttg cgtaaaagtg tcggaccgag ttactaacac taccgtgacc tacgattccc    69540
tagcattcga agggcgctta gccctaaacg ctaccaccct ccgctggagc tcttcagtac    69600
tggaaacagc cgcgcttgat gtggtatctc tgttttctga ggacgtccgt atagatgttc    69660
cagtggcaga gaaaacggta gacaagtatg agtaacacgg aattaggaat cggtgatacc    69720
gtggaggtga ttgtcactgc caatcacttc ctagagaaat tttgtagagt gggtcgtatt    69780
actaagaagc atggctcatt ctactgggta aagttcaagt ttaactttag taacgacaat    69840
aagcatttgc actgttacga ccagattgac ttcggaccat ttagcatcaa ccaattaaaa    69900
ctgttggaga aaaataccaa tgacacaagc agcgaagaaa gtactaagcc taacggacat    69960
catcggaaag ttcgcaggca gcgtaatcga gttgaaccag aacaagtttc ccgcaaacct    70020
agaaagcgtc gtgcaagact tagcacacca ctttaagttc ttctcacaaa acctaggcgg    70080
cgtagatatg gtggactaca gccgtggtga gttttacgac ttactacacg agtacatcat    70140
ggcagacgtc cgctgtgaag agtggaatcg ccccgacggt gaagggcact ttatcgacct    70200
agttgcactt gtgcagaacg tgacttacgc cctctatggt ccgctaagcg ttgtccatga    70260
agtaccacca gagaatgatt actcacgctt ggattcattc gatagtaaga agcaggtgcg    70320
tgcagcggtg atcgcatcgt actcgattga agactgtgaa gtgactgtcc acgtggaagg    70380
cgacgaccag tacccactag agacaatcaa agtaacccac gacttcttcg cccgtgctgt    70440
```

| | | | | | |
|---|---|---|---|---|---|
| accagtggcg | gaccagtcag | ttttagtaat | ctacgagaac | ggctatcagt | cgcacagtcc | 70500 |
| actcgatgta | ttcaaagctg | gtcacgtacg | ttcattcgct | atcaaagacc | cggcgtctac | 70560 |
| aatgcctccg | gcagcgtaca | tggacagctg | tgagatgacg | ctatcggaac | agtactttga | 70620 |
| gcctgacgct | acgatcatta | actgcatgaa | agagttcatc | attagtggta | acgttctgga | 70680 |
| tgggttcaag | aagtctatct | actacggcaa | agaagccccg | gtagttgact | tgatggaaaa | 70740 |
| gctagagcta | acagacatcg | cagactggcg | agcactaaac | ccacacgagc | agaaggtcct | 70800 |
| acatgccgtt | ctgggcatgg | ctacggagag | cacagagtta | gtcgagcaaa | tatacggcta | 70860 |
| catgttccaa | ggtaaggagc | tggacccttaa | gaacttgtac | gaagaagtag | gcgacaactt | 70920 |
| attctacgta | agcactatgc | tcaagtgcct | aggtgtttct | tacgagcagg | caatgtacga | 70980 |
| caaccacatg | aaacgcatga | agcgttacgc | aggtggtaag | ttctcaccag | aagcggcaat | 71040 |
| caaccgcgat | gtagaagcgg | agttgcaaca | gcttactaag | agtggtaatc | tagctgggca | 71100 |
| gtaaagtaaa | tcagcttcca | taactctatg | taggttccgg | gcttggacca | catgtttgag | 71160 |
| gtctccgaaa | ggggacctct | ttttttatct | gtagaatgta | ggtatcctat | cccccggtaa | 71220 |
| gtagcacttt | agttgacggg | gagccctatg | tcagaacaag | cagaagagaa | gccacgcaga | 71280 |
| cgtcgccagc | gcaagcagat | attgagcgtt | gcccagcgtc | gtctccagcg | cacgtggaag | 71340 |
| ctggatgaag | agacgaaaga | gagattcatc | gaagcgatcc | taaaaggcat | gagcgaagag | 71400 |
| cgtgcctgta | tgttagtaag | aatcaacaag | ctgcactact | tcgagaagaa | gaagaaagta | 71460 |
| cacgagtact | tgaactcagg | tattgagcct | acgggtgggg | acgacccacg | cagtaatatc | 71520 |
| gacgagtggg | ctatgttcat | tgaagaggtc | gaggcggcag | tagccgagca | tgagctaaac | 71580 |
| ctaatcgacg | acgccttaga | cattgattct | gagtcgaaga | acaagaacta | ctgggcgcgt | 71640 |
| aacatgacaa | tccttgaacg | tcgtaaccgt | acagactggg | gtcgtcagga | atctatcaca | 71700 |
| cacagcatcg | ggcactacga | cccggatgac | agattccttt | aatcttagta | aacaacctag | 71760 |
| ggagcttcgg | ctccctttc | ttttgggcgt | cgtataggtg | atcgtcacca | acaaagccta | 71820 |
| ggaggaatgg | catagtgaaa | gaacgttacc | gtgacgagct | cacgtggtgg | gagaagcgcc | 71880 |
| taggtgtttg | gcgagttaac | aaggactcat | acgacacaac | ttggggctac | ttcgcaccgc | 71940 |
| gctgggctct | ggagttcaag | ttcaatgcgg | gcgggtactt | tagtaaccag | tgctcgctag | 72000 |
| atgtggggtt | catctgggga | ctgtttcaca | ttaagctgcc | gatacgtctt | aagaaccacg | 72060 |
| aggagagctg | tgagtggaac | gactacggct | ttatgtggta | cgagaaccaa | tgggtattca | 72120 |
| aatgggggcga | gaagtctaag | tggtgggatg | ttccatttat | ctcatggacc | tttgactttc | 72180 |
| atcatgtaat | gcacaaagac | ggacattggg | taaatggcga | ccaagcgtgg | aagaacgagg | 72240 |
| agattgaaaa | agaaatcttt | gattacacgt | atgtattaga | gtccggggaa | gttcagcacc | 72300 |
| gcaaggcaac | ttgctaccgt | gagcgacgcc | agtggcaccg | taagtggctt | ccgttcctaa | 72360 |
| agcgtacagt | tacttcgatt | agtatcgagt | ttgatgacga | ggtgggggag | cgtagcggta | 72420 |
| cttggaaagg | cggtactatg | ggatgcggct | gggacctact | gcctaacgag | acaatcgagc | 72480 |
| agtgcttacg | ccgtatggag | aaagaacgca | agttcaccta | agcaacttt | taaccacgta | 72540 |
| taattaacag | caaccgggaa | taatcccttta | actttagtaa | aaaggaaact | ctaatgagta | 72600 |
| agaaactatt | agtaccatca | tttgcaactg | cgcttgtagc | attcaaagac | gaactactac | 72660 |
| agcgtgcggc | tgaagtgaag | cagaaagcgg | gtgaaatggc | ttttgacatc | ctaacaggtg | 72720 |
| gttcaactac | cgtagacact | gagaaggcaa | tctcgaatgc | tcaggcgct | gtgggtgcct | 72780 |
| acgagtttgc | gcatgaagcg | gtacaatcct | tactacaaca | cttcggtgta | gatggtgcga | 72840 |

```
tccatctggt cattgccggg gacttagact caattgtgat cgggaagcct aagaacgttc    72900
ctaccatgac cttgattacg tcacgcgacc tacacctagt agaaggtggt cacgtattcg    72960
tgcaggataa ggcaggcgag ttctacgtgc agatccagag tattactaag actgaaggca    73020
ccgccgatgt ttctccagag tttacctacg tggctaaaat cctaggtact ttgactccgg    73080
ggtacgtcga ggctacacca gcaacgtcta caggtcgtag ttcagcacgc aagccagctg    73140
ccgctaacaa gcctaagccg ggtaacaaaa ctgcaagcaa gccagcggct aagaacccac    73200
cacgctcacg taagccacgt ggtcagaagc cagaaacaaa gccagcggaa aaggcggcgg    73260
agaacggctc aaaaaacgcg gaagcggcaa gcagtcagga aggcgcaaac taaccaaagc    73320
tgacttgcca gtggaccgct ggagagtagc attcgatttg atgagtgcca attagtaaaa    73380
cctagggagc ttcggctccc ttttcgtgc ctaagtgcct aggtgttttc gacctaagtg    73440
cctaggtagt ttgagcctaa gtgcctaggc tgtttagtaa aaaccacccg atgccgggat    73500
tcccgtgatc gggcaggaag ccccgccccg tacagctttc cgctgaattt acacccttt    73560 ggtgatcacc cccggaactg aaaaatagtt caaaaaactg tttactatta gtaaaaaccg    73620
cgtatagtta accgggtaga caaggagcac gcaacaatgc acaaactact gaaggcttc    73680 acgctattac tcgcctcttt actaattatg ggcggtgatt caataataga cttagcctat    73740
aactttttta gtaatttatt ttagtaaagg tgttgactca ctaaaaacag tttagtaaag    73800
ttagcaacca gaaacacggt cactcattag taagaggaaa acggaaatga ctaaacgcgc    73860
ttcagaactt gccaaaaaca ctgcttttaa cgatttgttc gcttcaagca aaacgggctt    73920
caacgttgcc gaaatgaaag acggcgacaa ggttaagaaa gacttccgca cgtatgtaat    73980
ccacccgtcg gcaattcgtg taattgacgg ctttaactcc cgcatggatt acggcgatat    74040
tgaagagctg gcgatgagtc ttaaagccga gcacgaaaac accgggcagg cacttatcca    74100
accgttgatc ttgatgtcgg ttaagggcga gaaagacact tacgatctta tcgctgggca    74160
ccgtagaatt atggcggtgc agtggttgtg ggagaatcta cagtatgacg tgggcggctt    74220
gatggctcgc atctacaagt acgatacgcc ttaccaccac atgatcggcg ttaacatgcg    74280
cgagaatgac caaaagccac tgttaccgat tgaagaggcg atcaacttca agcgccttaa    74340
agatgcggat tacacgctgg agcagatccg agatcttagt ggtcgctcaa tctgtcatat    74400
tagtaagcgt ttaacgcttc taactggtgc ggacgaagtt gtggacgcgg tagcatccgg    74460
ggaacttcaa tcacaaatgg cggctgaaat tgtcgtacgt cgtaagggtg acatcgaagg    74520
acaaaaggag cttgtcaaga aagccacgga aagcaaggaa ggcaaccgcg ctgtacgcca    74580
gcaacttaag gcggaaatga actcaaccgg acgcaagaaa cgcgctaaga agcggagaa    74640 gaccggggac aaaggcgacg ttaaaaacaa gcgcctaact caaaaagagc atgacgaatt    74700
agtaacatct catgcgatgt gggcggctga ctttgtgaag acgtacggta tcccggttga    74760
tcaggtcgaa gtcatgaaaa aggcgggaga gttacgcgct gaaggtgacg ccgggtatcg    74820
taagcttact aagatgcttc aagaatttgg aaagattgac ggaatcgcgc ttgtgctagg    74880
catcgactta taaggtgcaa gtttaaccgg gtaattcgg tagggagctc ccccttatta    74940
gctccccttt ttaaagggct tccgtgcgga gtcttttaga aagatatacc actgctagcc    75000
gggtaattac ggcagggcta ccttacagcc cactttttaa agcgcattta gtaaagtgcg    75060
ttttagcaag tacaacaatc ggagtcagat aaatgctact agcaaaaaac ctacagcgtg    75120
cgccttacct taagacttta ggcgataccc ttttcgctca ctgcgtgcag gatctaccat    75180
```

-continued

```
tcacggcgct tgataccgcg ccagccttca cccttactat tactaagggc ggggacctag  75240
caacagctca cacgctggca atccgcgatg tggaggaggt ccacgatata gcccgccact  75300
ttaagaccgg ggctaaacgc ctacacggaa tccagatctt taatgacccg cttgctatct  75360
ttgagcagca cggcggtcac acgtggaccg ggaaggcgat ttataacgcg tttattgcca  75420
acagctcaac actgggcaag aaatggatca agcaagcgag cgcgtacgat attatgaaaa  75480
ctgtcaatac cgtcaatgat cgtgcgttta gtgtatgggt agaggaatta tgcgcaaagg  75540
tggaagaatg ctaaaacgct ctataatcgc cgctgtgctg tttttcagtg ctaacatggc  75600
tcatggtgcc actgactggc aaaacgttca atctgacgcg tttgcggcgc gatttgcggt  75660
acagtcaatg attccttctc gctgtattta cccggaacgc ttcaaccgct tctataaatc  75720
ggtgaaggct gacggttttg atactgcttt gctgaaggac gataaattcc ttactaagat  75780
taagcgcgag aaagctagtc ttaaaaagtg gctgggtaca actgacgacg gttgtgcaat  75840
cattagcaag caattcccta accagtatta caagggattc ttttaaacta ttttactaat  75900
tcggagactc gaatcatggc agacctacaa cttcctaaca caatcgcggc agcggctaag  75960
aatctaccaa acgaagcgcg tgcaatccta ttgcagaagt accgcgacca agctaagagc  76020
aagggcttga actgggtatg ctggctgttt ggtctacagc acttctacca aggcaagatc  76080
ggaacgggta tcctcttcct ttgtcttatc ccggtaggtg taagctttgt gtggtggatt  76140
attgaagcct tccgcaataa caagcagatt gaccgctata acgacacgct ggcaatggag  76200
ctgttcgcag agtctaagct gctagcaagc gactagctga aaagcctaag cacttcttac  76260
taataagcct cggaatgttc cggggctttt ttgatcgtgg atgcctagga aagataacat  76320
aatgcttata aaacctgaga cgctatcagt tcgcctagac gtaacccgcg tcctttcacc  76380
ccgctgcgct atcctgctgg cgataataca gcacacgtac gaccatagct gtgcgtccca  76440
caatgactgc cagatgcacg aaggcaagcg ttgggtacga atcagtaact ctgagttccg  76500
agagctaaca agctttagtc caaccacgat tactaaaagt atccaatccc tagtgtcgtt  76560
cagtatgatc gagactaaga ctcttactaa agataaaggt gatgtggcta actggttcac  76620
agtcagcaag gaggagtagt catgcgagcc ttccgacttc ccgata                76666
```

VIBRIO PARAHAEMOLYTICUS BACTERIOPHAGE VIB-PAP-4 AND USE THEREOF IN INHIBITING PROLIFERATION OF VIBRIO PARAHAEMOLITICUS BACTERIA

CROSS-REFERENCE TO RELATED APPLICATIONS

This application is a U.S. National Phase Application of International Application No. PCT/KR2017/013765, filed Nov. 29, 2017, which claims priority to Korean Application No. 10-2016-0175223, filed Dec. 21, 2016, each of which are hereby incorporated by reference in their entirety.

Reference to Sequence Listing

The Sequence Listing submitted Jun. 19, 2019 as a text file named "08162_0054U1_Sequence_Listing.txt," created on Jun. 18, 2019, and having a size of 97,533 bytes is hereby incorporated by reference pursuant to 37 C.F.R. § 1.52(e)(5).

TECHNICAL FIELD

The present invention relates to a bacteriophage isolated from nature, which infects *Vibrio parahaemolyticus* to thus kill *Vibrio parahaemolyticus*, and a method for preventing and treating a *Vibrio parahaemolyticus* infection using a composition including the same as an active ingredient. More particularly, the present invention relates to a *Myoviridae* bacteriophage Vib-PAP-4 (Accession number: KCTC 13168BP) isolated from nature, which has the ability to specifically kill *Vibrio parahaemolyticus* and which includes a genome expressed by SEQ. ID. NO: 1, and a method for preventing a *Vibrio parahaemolyticus* infection and a treatment method after the *Vibrio parahaemolyticus* infection using a composition including the bacteriophage as an active ingredient.

BACKGROUND ART

*Vibrio parahaemolyticus*, belonging to the genus *Vibrio*, is a facultative anaerobe having peritrichous flagellum, and is a gram-negative bacterium. It is known as representative causative bacteria of food-borne infectious diseases, which are common in Japan and Southeast Asia including Korea. Most *Vibrio parahaemolyticus* are non-pathogenic, and only *Vibrio parahaemolyticus* exhibiting a hemolytic phenomenon is pathogenic. Serologically, it is classified according to 13 types of somatic antigens (O) and 75 types of capsular antigens (K). New K antigen types are added every year and flagella antigens (H) are present in all *Vibrio parahaemolyticus*. Therefore, the serotype of *Vibrio parahaemolyticus* is classified depending on the type of O and K antigens.

*Vibrio parahaemolyticus* causes serious economic damage in the aquaculture industry by causing vibriosis in various fishes and shellfishes. In particular, outbreaks of vibriosis in fish caused by a *Vibrio parahaemolyticus* infection occur frequently, resulting in great economic damage. Therefore, there is an urgent need to develop a method that is applicable for preventing and further treating a *Vibrio parahaemolyticus* infection.

Antibiotics are extensively used for the inhibition and treatment of infections caused by *Vibrio parahaemolyticus*. Recently, the effectiveness of antibiotics has been continuously decreasing due to the increase of antibiotic-resistant bacteria, and the development of effective methods other than antibiotics is required due to the increased number of regulations on the use of antibiotics in cultured fish. Especially, there is a great demand for environmentally friendly methods.

Recently, the use of bacteriophages as a countermeasure against bacterial diseases has attracted considerable attention. In particular, interest in bacteriophages is higher than ever due to the preference of environmentally friendly methods. Bacteriophages are very small microorganisms infecting bacteria and are usually simply called "phages". Once a bacteriophage infects bacteria, the bacteriophage is proliferated in the inside of the bacterial cell. After proliferation, the progeny of the bacteriophage destroys the bacterial cell wall and escapes from bacteria as the host, suggesting that the bacteriophage has the ability to kill bacteria.

The manner in which the bacteriophage infects bacteria is characterized by very high specificity thereof, so that the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria and does not affect commensal bacteria in the environment or in the intestines of fish. Conventional antibiotics, which have been widely used for bacterial treatment, influence many kinds of bacteria coincidentally. This causes problems such as environmental pollution or the disturbance of normal flora in animals. On the other hand, the use of bacteriophages does not disturb normal flora in animals, because the target bacterium is killed selectively. Hence, the bacteriophage may be utilized safely, which thus greatly lessens the probability of adverse actions in use compared to any other conventional antibiotics.

Bacteriophages were first discovered by the English bacteriologist Frederick Twort in 1915 when he noticed that *Micrococcus* colonies melted and became transparent by something unknown. In 1917, the French bacteriologist Felix d'Herelle discovered that *Shigella dysenteriae* in the filtrate of dysentery patient feces was melted by something, and further studied this phenomenon. As a result, he identified bacteriophages independently, and named them bacteriophages, which means "to eat bacteria". Since then, bacteriophages acting against such pathogenic bacteria as *Shigella, Salmonella Typhi*, and *Vibrio cholerae* have been continuously identified.

Owing to the unique ability of bacteriophages to kill bacteria, bacteriophages have attracted anticipation as an effective countermeasure against bacterial infection since their discovery, and there has been a lot of research related thereto. However, since penicillin was discovered by Alexander Fleming, studies on bacteriophages have continued only in some Eastern European countries and the former Soviet Union because the spread of antibiotics was generalized. Since 2000, the limitations of conventional antibiotics have appeared due to the increase in antibiotic-resistant bacteria, and the possibility of developing bacteriophages as a substitute for conventional antibiotics has been highlighted, so that bacteriophages are again attracting attention as anti-bacterial agents. In particular, recently, government regulations for the use of antibiotics have become more stringent around the world, and thus interest in bacteriophages is increasing and industrial applications therefor are increasingly arising.

As demonstrated above, bacteriophages tend to be highly specific for bacteria. Because of this specificity, bacteriophages frequently exhibit an antibacterial effect only for certain strains of bacteria, even though the bacteria belong to the same species. In addition, the different bacteriophages exhibit different antibacterial strengths against the same bacteria strain. Therefore, it is necessary to collect many kinds of bacteriophages that are useful to control specific bacteria efficiently. Hence, in order to develop the effective bacteriophage utilization method in response to *Vibrio parahaemolyticus*, many kinds of bacteriophages that exhibit antibacterial action against *Vibrio parahaemolyticus* must be acquired. Furthermore, the resulting bacteriophages need to be screened as to whether or not they are superior to others from the aspect of antibacterial strength and spectrum.

DISCLOSURE

Technical Problem

Therefore, the present inventors endeavored to develop a composition applicable for the prevention or treatment of a *Vibrio parahaemolyticus* infection using a bacteriophage that is isolated from nature and can selectively kill *Vibrio parahaemolyticus*, and further to establish a method for preventing or treating a *Vibrio parahaemolyticus* infection using the composition. As a result, the present inventors isolated a bacteriophage suitable for this purpose from nature and secured the gene sequence of the genome that distinguishes the isolated bacteriophage from other bacteriophages. Then, the present inventors developed a composition including the bacteriophage as an active ingredient, and identified that this composition could be efficiently used to prevent and treat a *Vibrio parahaemolyticus* infection, leading to the completion of the present invention.

Accordingly, it is an object of the present invention to provide a *Myoviridae* bacteriophage Vib-PAP-4 (Accession number: KCTC 13168BP) isolated from nature, which has the ability to specifically kill *Vibrio parahaemolyticus* and which includes the genome expressed by SEQ. ID. NO: 1.

It is another object of the present invention to provide a composition applicable for preventing *Vibrio parahaemolyticus* infection, which includes a bacteriophage Vib-PAP-4 infecting *Vibrio parahaemolyticus* to thus kill *Vibrio parahaemolyticus* as an active ingredient, and a method for preventing a *Vibrio parahaemolyticus* infection using said composition.

It is another object of the present invention to provide a composition applicable for treating a *Vibrio parahaemolyticus* infection, which includes a bacteriophage Vib-PAP-4 infecting *Vibrio parahaemolyticus* to thus kill *Vibrio parahaemolyticus* as an active ingredient, and a method for treating a *Vibrio parahaemolyticus* infection using said composition.

It is another object of the present invention to provide a medicine bath agent (immersion agent) for preventing and treating a *Vibrio parahaemolyticus* infection using said composition.

It is another object of the present invention to provide a feed additive effective upon farming by preventing and treating a *Vibrio parahaemolyticus* infection using said composition.

Technical Solution

The present invention provides a *Myoviridae* bacteriophage Vib-PAP-4 (Accession number: KCTC 13168BP) isolated from nature, which has the ability to specifically kill *Vibrio parahaemolyticus* and which includes a genome expressed by SEQ. ID. NO: 1, and a method for preventing and treating *Vibrio parahaemolyticus* infection using a composition including the same as an active ingredient.

The bacteriophage Vib-PAP-4 was isolated by the present inventors and then deposited under the Budapest Treaty on the International Procedure at Korean Collection for Type Cultures, Korea Research Institute of Bioscience and Biotechnology (KRIBB), 125 Gwahak-ro, Yuseong-gu, Daijeon 305-806, Republic of Korea; the deposit was made on Dec. 2, 2016 (Accession number: KCTC 13168BP).

The present invention also provides a medicine bath agent and a feed additive applicable for the prevention or treatment of a *Vibrio parahaemolyticus* infection, which include the bacteriophage Vib-PAP-4 as an active ingredient.

Since the bacteriophage Vib-PAP-4 included in the composition of the present invention kills *Vibrio parahaemolyticus* efficiently, it is regarded effective in the prevention (prevention of infection) or treatment (treatment of infection) of diseases caused by *Vibrio parahaemolyticus*. Therefore, the composition of the present invention can be utilized for the prevention and treatment of diseases caused by *Vibrio parahaemolyticus*.

In this description, the term "prevention" or "prevent" indicates (i) to block a *Vibrio parahaemolyticus* infection; and (ii) to inhibit the development of diseases caused by a *Vibrio parahaemolyticus* infection.

In this description, the term "treatment" or "treat" indicates all actions that (i) suppress diseases caused by *Vibrio parahaemolyticus*; and (ii) alleviate the pathological condition of the diseases caused by *Vibrio parahaemolyticus*.

In this description, the term "isolate", "isolating", or "isolated" indicates actions which isolate bacteriophages from nature by applying diverse experimental techniques and which secure characteristics that can distinguish the target bacteriophage from others, and further includes the action of proliferating the target bacteriophage using bioengineering techniques so that the target bacteriophage is industrially applicable.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Vib-PAP-4 is included as an active ingredient. The bacteriophage Vib-PAP-4 is included at a concentration of $1 \times 10^1$ pfu/ml to $1 \times 10^{30}$ pfu/ml or $1 \times 10^1$ pfu/g to $1 \times 10^{30}$ pfu/g, and preferably at a concentration of $1 \times 10^4$ pfu/ml to $1 \times 10^{15}$ pfu/ml or $1 \times 10^4$ pfu/g to $1 \times 10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. The formulation may be in the form of a solution, suspension, or emulsion in oil or a water-soluble medium, extract, powder, granule, tablet, or capsule. A dispersing agent or stabilizer may be additionally included.

The composition of the present invention may be prepared as a medicine bath agent and a feed additive according to the purpose of use, without limitation thereto.

For this purpose, bacteriophages that confer antibacterial activity against other bacterial species may be further included in the composition of the present invention in order to improve the effectiveness thereof. In addition, other kinds of bacteriophages that have antibacterial activity against *Vibrio parahaemolyticus* may be further included in the composition of the present invention. These bacteriophages may be combined properly so as to maximize antibacterial effects, because their antibacterial activities against *Vibrio parahaemolyticus* may be different from the aspects of antibacterial strength and spectrum.

Advantageous Effects

The method for preventing and treating *Vibrio parahaemolyticus* infection using the composition including the bacteriophage Vib-PAP-4 as an active ingredient according to the present invention may have the advantage of very high specificity for *Vibrio parahaemolyticus*, compared with the conventional methods based on chemical materials including conventional antibiotics. This means that the composition can be used for preventing or treating the *Vibrio parahaemolyticus* infection without affecting other commensal bacteria that are useful and has fewer side effects according to the use thereof. In general, when chemical materials such as antibiotics are used, commensal bacteria are also damaged, thus weakening immunity in animals and entailing various side effects owing to the use thereof. Further, the composition of the present invention uses a bacteriophage isolated from nature as an active ingredient, and thus it is very environmentally friendly. Meanwhile, in the case of bacteriophages exhibiting antibacterial activity against the same species of bacteria, the antibacterial activities of the bacteriophages are different with regard to antibacterial strength and spectrum [the spectrum of the antibacterial activity of the bacteriophages applied to individual bacteria strains in terms of the strains of various bacteria belonging to *Vibrio parahaemolyticus*. Typically, bacteriophages are usually effective only on some bacterial strains, even within the same species. That is to say, the antibacterial activity of bacteriophage may depend on the bacterial strain even for the same species of bacteria]. Accordingly, the present invention may provide antibacterial activity against *Vibrio parahaemolyticus* different to that provided by other bacteriophages acting on *Vibrio parahaemolyticus*. This provides significantly different applicability to industrial fields.

DESCRIPTION OF DRAWINGS

FIG. 1 is an electron micrograph showing the morphology of the bacteriophage Vib-PAP-4.

FIG. 2 is a photograph showing the results of an experiment on the ability of the bacteriophage Vib-PAP-4 to kill *Vibrio parahaemolyticus*. Based on the center line of the plate culture medium, only the buffer containing no Bacteriophage Vib-PAP-4 is spotted on the left side thereof, and a solution containing Bacteriophage Vib-PAP-4 is spotted on the right side thereof. The clear zone observed in the right side is a plaque formed by lysis of the target bacteria due to the action of Bacteriophage Vib-PAP-4.

MODE FOR INVENTION

Hereinafter, the present invention will be described in more detail with reference to Examples. However, the Examples are merely examples of the present invention, and the scope of the present invention is not limited to the Examples.

Example 1: Isolation of Bacteriophage Capable of Killing *Vibrio parahaemolyticus*

Samples were collected from nature to isolate the bacteriophage capable of killing *Vibrio parahaemolyticus*. Meanwhile, the *Vibrio parahaemolyticus* used for the bacteriophage isolation were distributed from Culture Collection of Antimicrobial Resistant Microbes (Distribution number: CCARM 0135).

The isolation procedure of the bacteriophage is described in detail hereinafter. The collected sample was added to an LB (Luria-Bertani) culture medium (tryptone, 10 g/L; yeast extract, 5 g/L; sodium chloride, 10 g/L) inoculated with *Vibrio parahaemolyticus* at a ratio of 1/1,000, followed by shaking culture at 37° C. for 3 to 4 hours. Upon completion of the culture, centrifugation was performed at 8,000 rpm for 20 minutes and a supernatant was recovered. The recovered supernatant was inoculated with *Vibrio parahaemolyticus* at a ratio of 1/1,000, followed by shaking culture at 37° C. for 3 to 4 hours. When the sample contained the bacteriophage, the above procedure was repeated a total of 5 times in order to sufficiently increase the number (titer) of the bacteriophages. After repeating the procedure 5 times, the culture solution was subjected to centrifugation at 8,000 rpm for 20 minutes. After the centrifugation, the recovered supernatant was filtered using a 0.45 μm filter. The obtained filtrate was used in a typical spot assay for examining whether or not a bacteriophage capable of killing *Vibrio parahaemolyticus* was included therein.

The spot assay was performed as follows: LB culture medium was inoculated with *Vibrio parahaemolyticus* at a ratio of 1/1,000, followed by shaking culture at 37° C. overnight. 3 ml ($OD_{600}$ of 1.5) of the culture solution of *Vibrio parahaemolyticus* prepared above was spread on LA (Luria-Bertani Agar: tryptone, 10 g/L; yeast extract, 5 g/L; sodium chloride, 10 g/L; agar, 15 g/L) plate. The plate was left on a clean bench for about 30 minutes to dry the spread solution. After drying, 10 μl of the prepared filtrate was spotted onto the plate which *Vibrio parahaemolyticus* was spread and then left for about 30 minutes to dry. After drying, the plate that was subjected to spotting was standing-cultured at 37° C. for one day, and then examined for the formation of a clear zone at the position at which the filtrate was dropped. In the case of the filtrate generating the clear zone, it is judged that the bacteriophage capable of killing *Vibrio parahaemolyticus* is included therein. Through the above examination, the filtrate containing the bacteriophage having the ability to kill *Vibrio parahaemolyticus* could be obtained.

The pure bacteriophage was isolated from the filtrate confirmed above to have the bacteriophage capable of killing *Vibrio parahaemolyticus*. A conventional plaque assay was used for the isolation of the pure bacteriophage. In detail, a plaque formed in the course of the plaque assay was recovered using a sterilized tip, which was then added to the culture solution of *Vibrio parahaemolyticus*, followed by culturing at 37° C. for 4 to 5 hours. After the culturing, centrifugation was performed at 8,000 rpm for 20 minutes to obtain a supernatant. The *Vibrio parahaemolyticus* culture solution was added to the obtained supernatant at a volume ratio of 1/50, followed by culturing at 37° C. for 4 to 5 hours. In order to increase the number of bacteriophages, the above procedure was repeated at least 5 times. Then, centrifugation was performed at 8,000 rpm for 20 minutes to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, the solution containing the pure bacteriophage was obtained. The procedure for the isolation of the pure bacteriophage was generally repeated until the generated plaques became similar to each other in size and morphology. In addition, the final isolation of the pure bacteriophage was confirmed using electron microscopy. Until the isolation of the pure bacteriophage was confirmed using the electron microscopy, the above procedure was repeated. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel above bacteriophage was confirmed to belong to the *Myoviridae* bacteriophage.

The solution containing the pure bacteriophage confirmed above was subjected to the following purification process. The *Vibrio parahaemolyticus* culture solution was added to the solution containing the pure bacteriophage at a volume ratio of 1/50 based on the total volume of the bacteriophage solution, followed by further culturing for 4 to 5 hours. After the culturing, centrifugation was performed at 8,000 rpm for 20 minutes to obtain a supernatant. This procedure was repeated a total of 5 times to obtain a solution containing sufficient numbers of the bacteriophage. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, and then left at 4° C. for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM $MgSO_4$, 0.1% Gelatin, pH 8.0). The resulting material was referred to as a bacteriophage suspension or bacteriophage solution.

As a result, the pure bacteriophage purified above was collected, was named the bacteriophage Vib-PAP-4, and was then deposited at Korean Collection for Type Cultures, Korea Research Institute of Bioscience and Biotechnology on Dec. 2, 2016 (Accession number: KCTC 13168BP).

Example 2: Separation and Sequence Analysis of Genome of Bacteriophage Vib-PAP-4

The genome of the bacteriophage Vib-PAP-4 was separated as follows. The genome was separated from the bacteriophage suspension obtained using the same method as in Example 1. First, in order to eliminate DNA and RNA of *Vibrio parahaemolyticus* included in the suspension, 200 U of each of DNase I and RNase A was added to 10 ml of the bacteriophage suspension and then left at 37° C. for 30 minutes. After being left for 30 minutes, in order to inactivate the DNase I and RNase A activity, 500 μl of 0.5 M ethylenediaminetetraacetic acid (EDTA) was added thereto and then left for 10 minutes. In addition, the resulting mixture was further left at 65° C. for 10 minutes, and 100 μl of proteinase K (20 mg/ml) was then added thereto so as to break the outer wall of the bacteriophage, followed by reaction at 37° C. for 20 minutes. After that, 500 μl of 10% sodium dodecyl sulfate (SDS) was added thereto, followed by reaction at 65° C. for 1 hour. After the reaction for 1 hour, 10 ml of the solution of phenol:chloroform:isoamyl alcohol mixed at a component ratio of 25:24:1 was added to the reaction solution, followed by mixing well. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the genome of the bacteriophage Vib-PAP-4.

Information on the sequence of the genome of the bacteriophage Vib-PAP-4 obtained above was secured by performing next-generation sequencing analysis using Roche 454 GS Junior equipment from ChunLab, Inc. The finally analyzed genome of the bacteriophage Vib-PAP-4 had a size of 76,666 bp and the sequence of the whole genome was expressed by SEQ. ID. NO: 1.

The homology (similarity) of the bacteriophage Vib-PAP-4 genomic sequence obtained above with previously reported bacteriophage genomic sequences was investigated using BLAST on the web. As a result of the BLAST investigation, it was confirmed that the genomic sequence of the bacteriophage Vib-PAP-4 had relatively high homology with the sequence of the *Vibrio* bacteriophage SSP002 (Genbank Accession No. JQ692107.1) and the sequence of the *Vibrio* bacteriophage vB_VpaS_MAR10 (Genbank Accession No. JX556418.1) (95%/98% and 69%/79%, respectively, in the order of query coverage/identity). However, the number of open reading frames (ORF) on the bacteriophage Vib-PAP-4 genome is 106, whereas the number in the case of bacteriophage SSP002 is 102 and the number in the case of *Vibrio* bacteriophage vB_VpaS_MAR10, having slightly low homology therewith is 104, confirming that they were different bacteriophages.

Based upon this result, it is concluded that the bacteriophage Vib-PAP-4 must be a novel bacteriophage that has not been reported previously. Further, since the antibacterial strength and spectrum of bacteriophages typically depend on the type of bacteriophage, it is considered that the bacteriophage Vib-PAP-4 can provide antibacterial activity different from that of any other bacteriophages reported previously.

Example 3: Investigation of Ability of Bacteriophage Vib-PAP-4 to Kill *Vibrio parahaemolyticus*

The ability of the isolated bacteriophage Vib-PAP-4 to kill *Vibrio parahaemolyticus* was investigated. In order to investigate the killing ability, the formation of clear zones was observed using the spot assay in the same manner as described in Example 1. A total of 23 strains of *Vibrio parahaemolyticus* were used for the investigation of killing ability and included 22 strains which were isolated and identified as *Vibrio parahaemolyticus* by the present inventors and 1 strain which was distributed from Culture Collection of Antimicrobial Resistant Microbes (*Vibrio parahaemolyticus* CCARM 0135). The bacteriophage Vib-PAP-4 had the ability to kill a total of 22 strains of *Vibrio para-* haemolyticus, including a *Vibrio parahaemolyticus* CCARM 0135 strain, among 23 strains of *Vibrio parahaemolyticus*, which was the experimental target. The representative experimental result is shown in FIG. 2. Meanwhile, the ability of the bacteriophage Vib-PAP-4 to kill *Edwardsiella tarda*, *Vibrio anguillarum*, *Vibrio ichthyoenteri*, *Lactococcus garvieae*, *Streptococcus parauberis*, *Streptococcus iniae*, and *Aeromonas salmonicida* was also investigated in a separate experiment. As a result, the bacteriophage Vib-PAP-4 did not have the ability to kill these microorganisms.

Therefore, it is confirmed that the bacteriophage Vib-PAP-4 has the specific ability to kill *Vibrio parahaemolyticus* and a broad antibacterial spectrum against *Vibrio parahaemolyticus*, suggesting that the bacteriophage Vib-PAP-4 can be used as an active ingredient of the composition for preventing and treating *Vibrio parahaemolyticus* infection.

Example 4: Experimental Example Regarding Prevention of *Vibrio parahaemolyticus* Infection Using Bacteriophage Vib-PAP-4

100 µl of a bacteriophage Vib-PAP-4 solution at a level of $1 \times 10^8$ pfu/ml was added to a tube containing 9 ml of an LB culture medium. To another tube containing 9 ml of an LB culture medium, only the same amount of LB culture medium was further added. A *Vibrio parahaemolyticus* culture solution was then added to each tube so that absorbance reached about 0.5 at 600 nm. After *Vibrio parahaemolyticus* was added, the tubes were transferred to an incubator at 37° C., followed by shaking culture, during which the growth of *Vibrio parahaemolyticus* was observed. As presented in Table 1, it was observed that the growth of *Vibrio parahaemolyticus* was inhibited in the tube to which the bacteriophage Vib-PAP-4 solution was added, while the growth of *Vibrio parahaemolyticus* was not inhibited in the tube to which the bacteriophage solution was not added.

TABLE 1

Growth inhibition of *Vibrio parahaemolyticus*

| | $OD_{600}$ absorbance value | | |
| --- | --- | --- | --- |
| Classification | 0 minutes after culture | 60 minutes after culture | 120 minutes after culture |
| Bacteriophage solution is not added | 0.498 | 1.023 | 1.684 |
| Bacteriophage solution is added | 0.498 | 0.261 | 0.182 |

The above results indicate that the bacteriophage Vib-PAP-4 of the present invention not only inhibits the growth of *Vibrio parahaemolyticus* but also has the ability to kill *Vibrio parahaemolyticus*. Therefore, it is concluded that the bacteriophage Vib-PAP-4 can be used as an active ingredient of the composition for preventing a *Vibrio parahaemolyticus* infection.

Example 5: Animal Experiment on Prevention of *Vibrio parahaemolyticus* Infection Using Bacteriophage Vib-PAP-4

The preventive effect of the bacteriophage Vib-PAP-4 on sea bass subjected to *Vibrio parahaemolyticus* infection was investigated. A total of 2 groups of sixty juvenile sea bass per group (body weight: 5 to 7 g and body length: 8 to 10 cm) was prepared and farmed separately in water tanks, and an experiment was performed for 14 days. The environment surrounding the water tanks was controlled, and the temperature in the laboratory where the water tanks were located was maintained constant. Over the whole experimental period from the $1^{st}$ day of the experiment, sea bass in an experimental group (the group to which the bacteriophage was administered) were fed with a feed containing the bacteriophage Vib-PAP-4 at $1 \times 10^8$ pfu/g according to a conventional feeding method. In contrast, sea bass in a control group (the group to which the bacteriophage was not administered) were fed with the same feed as in the experimental group except that the bacteriophage Vib-PAP-4 was not contained according to the same method as in the experimental group. From the $7^{th}$ day after the experiment started, the feed to be provided was contaminated with *Vibrio parahaemolyticus* at a level of $1 \times 10^8$ cfu/g for two days and thereafter provided respectively twice a day so as to induce a *Vibrio parahaemolyticus* infection. From the $9^{th}$ day after the experiment started (the $2^{nd}$ day after the *Vibrio parahaemolyticus* infection was induced), vibriosis pathogenesis was examined in all test animals on a daily basis. The vibriosis pathogenesis was examined by measuring a body darkening index. The measurement of the body darkening index was performed using a conventional method for measuring a dark coloration (DC) score (0: normal, 1: slight darkening, 2: strong darkening). The results are shown in Table 2.

TABLE 2

Result of measurement of body darkening index (mean)

| | DC score (mean) Days | | | | | |
| --- | --- | --- | --- | --- | --- | --- |
| | D 9 | D 10 | D 11 | D 12 | D 13 | D 14 |
| Control group (bacteriophage is not administered) | 0.67 | 0.70 | 0.73 | 0.93 | 1.07 | 1.20 |
| Experimental group (bacteriophage is administered) | 0.17 | 0.03 | 0.03 | 0.03 | 0 | 0 |

From the above results, it is confirmed that the bacteriophage Vib-PAP-4 of the present invention could be very effective in inhibiting *Vibrio parahaemolyticus* infection.

Example 6: Example of Treatment of Infectious Diseases of *Vibrio parahaemolyticus* Using Bacteriophage Vib-PAP-4

The treatment effect of the bacteriophage Vib-PAP-4 on sea bass suffering from vibriosis caused by *Vibrio parahaemolyticus* was investigated. A total of 2 groups of sixty juvenile sea bass per group (body weight: 5 to 7 g and body length: 8 to 10 cm) was prepared and farmed separately in water tanks, and an experiment was performed for 14 days. The environment surrounding the water tanks was controlled, and the temperature in the laboratory where the water tanks were located was maintained constant. From the $5^{th}$ day after the experiment started, the feed contaminated with *Vibrio parahaemolyticus* at a level of $1 \times 10^8$ cfu/g was provided twice a day for three days according to a conventional feeding method. Sea bass subjects showing clinical symptoms of vibriosis were observed in both water tanks from the last day of the procedure in which the feed contaminated with *Vibrio parahaemolyticus* was provided. From the next day after the feed contaminated with *Vibrio parahaemolyticus* was provided for three days (the $8^{th}$ day after the experiment started), sea bass in an experimental group (the group to which the bacteriophage was administered) were fed with a feed containing the bacteriophage Vib-PAP-4 ($1\times10^8$ pfu/g) according to a conventional feeding method. In contrast, sea bass in a control group (the group to which the bacteriophage was not administered) were fed with the same feed as in the experimental group except that the bacteriophage Vib-PAP-4 was not contained according to the same method as in the experimental group. From the $3^{rd}$ day after the forced infection of *Vibrio parahaemolyticus* (the $8^{th}$ day after the experiment started), vibriosis pathogenesis was examined in all test animals on a daily basis. The vibriosis pathogenesis caused by *Vibrio parahaemolyticus* was examined by measuring a body darkening index as in Example 5. The results are shown in Table 3.

TABLE 3

Result of measurement of body darkening index (mean)

| | DC score (mean) Days | | | | | | |
|---|---|---|---|---|---|---|---|
| | D 8 | D 9 | D 10 | D 11 | D 12 | D 13 | D 14 |
| Control group (bacteriophage is not administered) | 0.87 | 1.00 | 1.07 | 1.17 | 1.27 | 1.33 | 1.37 |
| Experimental group (bacteriophage is administered) | 0.83 | 0.77 | 0.73 | 0.57 | 0.37 | 0.20 | 0.17 |

From the above results, it is confirmed that the bacteriophage Vib-PAP-4 of the present invention could be very effective in the treatment of infectious diseases caused by *Vibrio parahaemolyticus*.

Example 7: Preparation of Feed Additives and Feeds

Feed additives were prepared using a bacteriophage Vib-PAP-4 solution so that a bacteriophage Vib-PAP-4 was contained in an amount of $1\times10^8$ pfu per 1 g of the feed additives. The method of preparing the feed additives was as follows: Maltodextrin (50%, w/v) was added to the bacteriophage solution and the resulting mixture was then freeze-dried. Finally, the dried mixture was ground into fine powders. In the above-described preparation procedure, the drying procedure can be replaced with drying under a reduced pressure, drying with heat, or drying at room temperature. In order to prepare the control for comparison, the feed additive that did not contain the bacteriophage but contained a buffer (10 mM Tris-HCl, 10 mM $MgSO_4$, 0.1% Gelatin, pH 8.0) used to prepare the bacteriophage solution was prepared.

The two kinds of feed additives that were prepared above were each mixed with a raw fish-based moist pellet at a weight ratio of 250, thus preparing two kinds of final feeds.

Example 8: Preparation of Medicine Bath Agent

The method of preparing a medicine bath agent was as follows: The medicine bath agent was prepared using a bacteriophage Vib-PAP-4 solution so that a bacteriophage Vib-PAP-4 was contained in an amount of $1\times10^8$ pfu per 1 ml of the medicine bath agent. In the method of preparing the medicine bath agent, the bacteriophage Vib-PAP-4 solution was added so that the bacteriophage Vib-PAP-4 was contained in an amount of $1\times10^8$ pfu per 1 ml of a buffer used to prepare the bacteriophage solution, and mixing was sufficiently performed. In order to prepare the control for comparison, the buffer used to prepare the bacteriophage solution was used as the medicine bath agent that did not contain the bacteriophage.

The two prepared kinds of medicine bath agents were diluted with water at a volume ratio of 1,000, resulting in the final medicine bath agent.

Example 9: Confirmation of Feeding Effect on Sea Bass Farming

Improvement in the feeding result upon sea bass farming was investigated using the feeds and the medicine bath agents prepared in Examples 7 and 8. In particular, the investigation was focused on mortality. A total of 1,000 juvenile sea bass was divided into two groups, each including 500 sea bass (group A; fed with the feed and group B; treated with the medicine bath agent), and an experiment was performed for four weeks. Each group was divided into sub-groups each including 250 sea bass, and the sub-groups were classified into a sub-group to which the bacteriophage Vib-PAP-4 was applied (sub-group-①) and a sub-group to which the bacteriophage was not applied (sub-group-②). In the present experiment, the target sea bass was the juvenile (body weight: 5 to 7 g and body length: 8 to 10 cm), and the juvenile sea bass of the experimental sub-groups were farmed in separate water tanks placed apart from each other at a certain space interval. The sub-groups were classified and named as shown in Table 4.

TABLE 4

Sub-group classification and expression in sea bass feeding experiment

| | Sub-group classification and expression | |
|---|---|---|
| Application | Bacteriophage Vib-PAP-4 is applied | Bacteriophage is not applied |
| Group fed with feed | A-① | A-② |
| Group treated with medicine bath agent | B-① | B-② |

In the case of provision of the feeds, the feeds prepared in Example 7 were provided according to a conventional feeding method as classified in Table 4. The treatment using the medicine bath agent was performed according to a conventional treatment method using a medicine bath agent, in which fish bodies are immersed in a diluted solution of the medicine bath agent, as classified in Table 4 using the medicine bath agent prepared as described in Example 8. The results are shown in Table 5.

TABLE 5

Mortality of sea bass in feeding experiment

| Group | Dead sea bass/total sea bass of experiment (No.) | Mortality (%) |
|---|---|---|
| A-① | 11/250 | 4.4 |
| A-② | 42/250 | 16.8 |
| B-① | 13/250 | 5.2 |
| B-② | 57/250 | 22.8 |

The above results indicate that the provision of the feed prepared according to the present invention and the treatment using the medicine bath agent prepared according to the present invention were effective in improving the feeding result in the farming of sea bass. Therefore, it is concluded that the composition of the present invention could be efficiently applied to improving the results of animal feeding.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

[Accession Number]
Name of Depositary Authority: KCTC
Accession number: KCTC 13168BP
Accession date: 20161202

The invention claimed is:

1. A composition for blocking a *Vibrio parahaemolyticus* infection, inhibiting the development of diseases caused by a *Vibrio parahaemolyticus* infection, suppressing diseases caused by *Vibrio parahaemolyticus*, or alleviating the pathological condition of the diseases caused by *Vibrio parahaemolyticus*, comprising:

maltodextrin and $1\times10^4$ pfu/g to $1\times10^{15}$ plaque-forming units per gram (pfu/g) of proliferated and purified *Myoviridae* bacteriophage Vib-PAP-4, which has an ability to specifically kill *Vibrio parahaemolyticus* and a genome represented by SEQ ID NO:1, and is deposited in the Korean Collection for Type Cultures (KCTC) under accession number KCTC 13168BP, wherein the maltodextrin and *Myoviridae* bacteriophage Vib-PAP-4 are in a dried mixture.

* * * * *